US008249698B2

(12) United States Patent
Mugler et al.

(10) Patent No.: US 8,249,698 B2
(45) Date of Patent: Aug. 21, 2012

(54) GENERAL DIAGNOSTIC AND REAL-TIME APPLICATIONS OF DISCRETE HERMITE FUNCTIONS TO DIGITAL DATA

(75) Inventors: Dale H. Mugler, Hudson, OH (US);
Soumyadipta Acharya, Baltimore, MD (US); Raghavan Gopalakrishnan, Parma, OH (US); Anandi Mahadevan, Akron, OH (US)

(73) Assignee: The University of Akron, Akron, OH (US)

( * ) Notice: Subject to any disclaimer, the term of this patent is extended or adjusted under 35 U.S.C. 154(b) by 1146 days.

(21) Appl. No.: 12/062,551

(22) Filed: Apr. 4, 2008

(65) Prior Publication Data

US 2008/0262367 A1    Oct. 23, 2008

Related U.S. Application Data

(63) Continuation-in-part of application No. 11/216,235, filed on Aug. 31, 2005, now abandoned.

(60) Provisional application No. 60/605,951, filed on Aug. 31, 2004.

(51) Int. Cl.
*A61B 5/0402* (2006.01)
*A61B 5/0476* (2006.01)
(52) U.S. Cl. ..................... 600/523; 600/544
(58) Field of Classification Search ............. 600/516, 600/517, 518, 519
See application file for complete search history.

(56) References Cited

U.S. PATENT DOCUMENTS

| | | | |
|---|---|---|---|
| 6,171,256 B1* | 1/2001 | Joo et al. ............ | 600/508 |
| 6,217,525 B1* | 4/2001 | Medema et al. ........ | 600/508 |
| 6,370,423 B1* | 4/2002 | Guerrero et al. ........ | 600/513 |
| 7,206,633 B2* | 4/2007 | Saba .................. | 607/14 |
| 2003/0050541 A1* | 3/2003 | Wuori ................. | 600/316 |
| 2003/0135097 A1* | 7/2003 | Wiederhold et al. ..... | 600/301 |
| 2005/0256413 A1* | 11/2005 | Astrom et al. .......... | 600/509 |
| 2005/0256745 A1* | 11/2005 | Dalton ................ | 705/3 |

OTHER PUBLICATIONS

Linh, Tran Hoai, Osowski, Stanislay, "On-Line Heart Beat recognition using hermite Polunomials and Neuro-Fuzzy Network", Aug. 2003, IEEE Transactions on Instrumentation and Measurments, vol. 52, No. 4, pp. 1224-1231.*

Allen, P.J., Pollizi, G., Krakow K., Fish, D.R. and Lemieux, L. (1998), "Identification of EEG events in the MR scanner: The problem of pulse artifact and a method for its subtraction". Neuroimage 8, 229-239.

Bonmassar, G., Purdon, P.L., Jaaskelainen, I.P., Chiappa, K., Solo, V., Brown, E.N. and Belliveau, J.W. (2002). "Motion and ballistocardiogram artifact removal for interleaved recording of EEG and Ep's during MRI". NeuroImage 16, 1127-1141.

(Continued)

*Primary Examiner* — Carl H. Layno
*Assistant Examiner* — Jon-Eric C. Morales
(74) *Attorney, Agent, or Firm* — Renner, Kenner, Greive, Bobak, Taylor & Weber

(57) ABSTRACT

General diagnostic and real-time application of digital Hermite functions allows features to be extracted from a measured signal through expansion of the measured signal. Specifically, the digital Hermite functions represent the shape of the measured signal in a set of vectors derived from a symmetrical tridiagonal matrix. This allows for efficient computation of the Hermite expansion coefficients, in real-time, to represent the expanded signal. The signal expansion also allows any artifacts, such as noise, to be isolated and removed, allowing the underlying signal of interest to be revealed.

23 Claims, 25 Drawing Sheets

OTHER PUBLICATIONS

Srivastava G., Crottaz-Herbette S., Lau K.M., Glover, G.H., and Menon, V., "ICA Based Procedures for Removing Ballistocardiogram Artifacts", From EEG Data Acquired in the MRI Scanner, NeuroImage 24, pp. 50-66 (2004).

T.H. Linh, et al, "On-line Heartbeat Recognition Using Hermite Polynomials and Neuro-fuzzy Network", from IEEE Transactions on Instrumentation and Measurement.

Jager, F., Mark R.G., Moody G.B., et al, "Analysis of Transient ST Segment Changes during Ambulatory ECG Monitoring using Karhunen-Loeve Transform", Proc. IEEE Comput. Cardiol pp. 691-694, 1992.

Jager F., Moody G., Mark R, "Detection of transient ST Segment Episodes during Ambulatory ECG Monitoring", Comput. Biomed Res., No. 31, pp. 305-322, 1998.

Baldilini F., Merri M., Benhorin J., et al. "Beat to Beat-Quantification and Anaylsis of ST Ddisplacement from Holter ECGs: A New Approach to Ischeima Detection", Proc. IEEE Comput. Cardiol., pp. 179-182, 1992.

Senhadji L., Carrault G., Bellanger J., et al. "Comparing Wavelet Transform for Recognizing Cardiac Pattern", IEEE Eng. Med. Biol., No. 14(2): pp. 167-173, 1995.

C. Papaloukas, D.I. Fotiadis, A. Likas, et al. "Use of a Novel Rule Based Expert System in the Detection of Changes in the ST Segment and T Wave in Long Duration ECGs", J. Electrocardiol., No. 35(1), pp. 105-112, 2001.

Vila J., Presedo J., Delagado M., et al. "SUTIL: Intelligent Ischemia Monitoring System", Int J. Med. Inf., No. 47(3), pp. 193-214, 1997.

Stamkopoulos T., Diamantaras K., Maglaveras N., et al. "CG Analysis Using Nonlinear PCA Neural Networks for Ischemia Beat Detection," IEEE Trans. Signal. Process, No. 46(11), pp. 3058-3067, 1998.

Maglaveras N., Stamkopoulos T., Diamantaras, K., et al., "ECG Pattern Recognition and Classification using Linear Transformations and Neural Networks: A Review", Intl. J. Med. Inf., No. 52, pp. 191-208, 1998.

* cited by examiner

GENERAL DIAGNOSTIC AND REAL-TIME APPLICATIONS OF DISCRETE HERMITE FUNCTIONS TO DIGITAL DATA

RELATED APPLICATION DATA

This application claims priority to previously filed U.S. Ser. No. 11/216,235, filed Aug. 31, 2005, entitled "Method and System for Evaluating Cardiac Ischemia", which claims priority to previously filed U.S. Provisional Application No. 60/605,951 filed on Aug. 31, 2004, entitled "Real Time Monitoring of Ischemic Changes in Electrocardiograms", both hereby incorporated by reference in their entirety.

FIELD OF THE INVENTION

The present invention relates to general diagnostic and real-time applications of discrete Hermite functions to digital data. More specifically, the invention relates to the application of discrete digital Hermite functions (DDHF) to biomedical data, for example, to extract features from digital signals, including but not limited to, ECGs, EMGs, EOGs, EEGs, and others. An automated system and method for real-time interpretation of any abnormalities present in a digital biomedical signal is provided. The word "discrete" here is used in the mathematical sense, and is interchangeable with the word "digital".

BACKGROUND OF THE INVENTION

The medical community, and the research community supporting the medical industry, strive to improve methods to assess and respond in a more timely manner to abnormalities identified by various measurement techniques. Often, seconds can mean the difference between life and death. Techniques used to measure abnormal functions in patients include, for example, ECGs, EMGs, EOGs, EEGs, and others. ECG measurements record heart function. EMG measurements record physiological properties of the muscles. EOG measurements record retinal data. EEG measurements record brain activity. Common among these analytical tools is the use of a means to record electrical data related to the function in question from the target organ or body system. Inherent in the measurement systems currently in use, however, are various drawbacks, including artifacts that mask or clutter recorded impulses or signals. Due to these and other drawbacks, complicated and cumbersome calculations are used to try and recover an accurate signal. These calculations are time consuming, causing a lapse between gathering the measured and recorded data and assessing malfunctions or abnormalities that are shown. This time lapse may be the difference between life and death for patients experiencing a critical episode.

Attempts have been made to address some of these drawbacks. For example, various non invasive measurements have been developed over the last few years to assess brain activity, and simultaneous recording of EEG-fMRI is one of them that is fast emerging as a tool in research and clinical studies related to neurophysiology. EEG signals reflect synchronous neuronal activity of the brain with a high temporal resolution in the order of milliseconds while fMRI measures the neural correlates using indirect means such as changes in blood oxygenation levels and has a very high spatial resolution (0.5-2 mm). These two types of data provide information complementary to each other Combined EEG-fMRI techniques are used to identify important spontaneous EEG activities, such as epileptic seizures, interictal spikes, the alpha rhythm, and sleep waves. It is also vital in identifying symptoms that change over short periods of time.

However, recording the EEG signal within the strong magnetic field of the MR scanner introduces two main types of artifacts: (i) one is due to the rapidly changing magnetic field or gradient known as the radiofrequency (RF) artifact; and (ii) the second is due to the small and tiny movements of the electrodes on the scalp because of the pulsatile changes in the blood flow coupled to the cardiac motion of the patient known as the ballistocardiogram (BCG). The BCG artifact is embedded within the EEG signal. It is highly non stationary in nature and varies slightly in shape and amplitude on a beat by beat basis, making it difficult to identify and remove. Moreover, it shares spectral components with the alpha and mu rhythm bands of the EEG signals. The elimination of the BCG artifacts is therefore particularly important in identification and study of various neurophysiologic disorders such as epileptic spikes, discharges and others.

The current methods for BCG artifact removal include Average Artifact Subtraction (AAS), Adaptive Filtering, and Independent Component Analysis (ICA). The most commonly used amongst them is the AAS method, wherein the average of the last 10 heartbeats is computed and this averaged waveform is subtracted from the original signal to give a clean record of the EEG signal. This was discussed in Allen, P. J., Pollizi, G., Krakow, K., Fish, D. R. and Lemieux, L. (1998), "Identification of EEG events in the MR scanner: The problem of pulse artifact and a method for its subtraction". Neuroimage 8, 229-239. However, this method relies heavily on the assumption of stationarity. The Adaptive Filtering methods, disclosed in Bonmassar, G., Purdon, P. L., Jaaskelainen, I. P., Chiappa, K., Solo, V., Brown, E. N. and Belliveau, J. W. (2002). "Motion and ballistocardiogram artifact removal for interleaved recording of EEG and Ep's during MRI". NeuroImage 16, 1127-1141, make use of a reference signal which is generally not commonly available in EEG-fMRI measurements. Additionally, this reference signal when acquired near the scalp does contain artifacts and cannot be treated as a standard reference signal. ICA techniques are shown to be successful in eliminating the BCG artifact but are computationally rigorous and exhaustive, making it difficult to implement in real time. See Srivastava G., Crottaz-Herbefte S., Lau K. M., Glover, G. H., and Menon, V., "ICA Based Procedures for Removing Ballistocardiogram Artifacts From EEG Data Acquired in the MRI Scanner", NeuroImage 24, pp. 50-66 (2004). Furthermore it relies on the assumption that the BCG artifact in each channel is a linear mixture of the underlying BCG sources, which is not necessarily true. There is a need for a mechanism which is capable of removing artifacts and promoting real-time assessment of recorded abnormalities.

Another example of a measurement technique that suffers from a lack of real-time assessment is in the area of heart health. Heart attacks and other ischemic events of the heart are among the leading causes of death and disability in the United States. In general, the susceptibility of a particular patient to heart attack or the like can be assessed by examining the heart for evidence of ischemia (insufficient blood flow to the heart tissue itself resulting in an insufficient oxygen supply) during periods of elevated heart activity. Of course, it is highly desirable that the measuring technique be sufficiently benign to be carried out without undue stress to the heart (the condition of which might not yet be known) and without undue discomfort to the patient.

The cardiovascular system responds to changes in physiological stress by adjusting the heart rate, which adjustments can be evaluated by measuring the surface ECG R-R intervals. The time intervals between consecutive R waves indicate the intervals between the consecutive heartbeats (RR intervals). This adjustment normally occurs along with corresponding changes in the duration of the ECG QT intervals, which characterize the duration of electrical excitation of cardiac muscle and represent the action potential duration averaged over a certain volume of cardiac muscle. Generally speaking, an average action potential duration measured as the QT interval at each ECG lead may be considered as an indicator of cardiac systolic activity varying in time.

Work has been done in the use of Hermite polynomials and neuro-fuzzy network used to recognize online heartbeat. See "On-line Heartbeat Recognition Using Hermite Polynomials and Neuro-fuzzy Network," by T. H. Linh, et al, IEEE Transactions on Instrumentation and Measurement. This work, however, is based on an analog technique which is not suitable for real-time analysis. The continuous functions used by Linh, et al are only orthogonal over an infinite domain, meaning that on a practical finite interval they are no longer orthogonal. Therefore, the results have an error in representing any real signal. Further, Linh, et al's formula for the coefficients is computationally intensive, involving the use of the "Singular Value Decomposition (SVD) and pseudo-inverse technique." That intensive computation results in Linh et al. using at most 15 coefficients in any given expansion, as computation of more coefficients would be time consuming using that method for the continuous case.

As is noted above, ischemic heart disease is a common cause of death and disability in industrialized countries. The ECG is one of the most important tools for the diagnosis of ischemia. Long term continuous ECG monitoring is found to offer more prognostic information than the standard 12 lead ECG, concerning ischemia. Given the usefulness of ECG in identifying ischemia, there is a need in the art for a reliable computer based method to interpret ECG results in order to identify the abnormalities associated with not only ischemia, but other types of heart disease as well.

What is lacking is a mechanism for accurately assessing measured functions, with the removal of artifacts and/or noise, in real-time, to assist in patient diagnosis and treatment. No assessment technique is currently available for the real-time evaluation of digital data, that is equally applicable to signals collected from a wide variety of measurement instruments used in a variety of biomedical disciplines, and that is capable of identifying and isolating a notable signal from an overall signal distorted by other factors, such as noise, artifacts, etc. Such a technique and method would enhance the capability of medical professionals relying on digital, electrical data to diagnose immediately the source of acute conditions in patients, not to mention the benefits to long-term treatment based on comparative data and assessment. The technique provided herein, based on the application of discrete Hermite functions to such digital data, provides the needed real-time assessment that is lacking in currently available systems.

SUMMARY OF THE INVENTION

The present invention relates to methods and systems for the use of dilated discrete Hermite functions to expand measured signals using a computationally efficient technique. These digital Hermite functions form the basis for the new discrete Hermite transform which provides information about the shape of the signals, such as that in the BCG artifact in an EEG or in an ECG interval. The Hermite transform coefficients generated on a beat by beat basis contain information unique to the shape features of the signal.

Therefore, in one embodiment the present invention relates to a method for the application of dilated discrete Hermite functions to biomedical data, the method comprising: gathering biomedical data comprising at least one electronic-based measured signal; expanding the electronic-based measured signal by application of the dilated discrete Hermite transform; extracting features using the transform relating to the electronic-based measured signal; and generating a new version of the electronic-based measured signal that includes only an underlying signal of interest present in the original electronic-based measured signal without unwanted noise.

In another embodiment, the present invention relates to an algorithm for BCG artifact removal making use of the dilated discrete Hermite transform to model the BCG accurately, followed by subtraction from the underlying EEG on a beat by beat basis to give an artifact free signal.

In another embodiment, the present invention relates to a method and system for evaluating abnormalities in electrocardiograms (ECGs), including abnormalities associated with cardiac ischemia. More particularly, the present invention relates to an automated system and method for interpreting any abnormalities present in an electrocardiogram (ECG), including those abnormalities associated with cardiac ischemia.

In still another embodiment, the present invention relates to a method for monitoring/detecting abnormalities in an ECG, the method comprising the steps of: (a) gathering at least one ECG; (b) subjecting the at least one ECG to a QRS detection algorithm in order to scan for R-peak location; (c) calculating the Hermite transform of the individual ECG complexes from each individual ECG; and (d) subjecting the Hermite coefficients to a Neural Network in order to determine the presence and/or absence of ECG abnormalities.

In yet another embodiment, the present invention relates to a method for identifying and removing artifacts from an EEG, including radiofrequency and BCG artifacts, in real-time, to improve critical assessment of data signals, the method comprising the steps of: (a) gathering at least one EEG over several heartbeats; (b) subjecting the at least one EEG to a detection algorithm in order to scan for BCG artifacts; (c) applying the algorithm for BCG artifact removal using the dilated discrete Hermite transform coefficients to model the BCG accurately; (d) subtracting the artifact from the underlying EEG on a beat-by-beat basis; and (e) recovering an artifact-free signal, all accomplished in real-time.

In addition to the applications already described, the discrete Hermite transform will find application to other signals of physiological interest. The values of the transform describe fundamental shapes present in a signal, as opposed to the discrete Fourier transform (and FFT fast computation method) that deals primarily with frequency analysis. The discrete Hermite transform can represent many features in biomedical signals with relatively few coefficients, so as to compress the amount of data that needs to be analyzed. Artifact removal, identification of important physiological features in a signal, or enhancement of particular features are all possible, and relate to important decisions that need to be made by doctors in analyzing a patient's illness. Those skilled in the art, using the teaching herein, will be able to apply the discrete Hermite transform to any electrical signal to achieve enhanced realization of a desired signal, or a notable signal, and to do so in real-time.

DETAILED DESCRIPTION OF THE INVENTION

Figure 1:
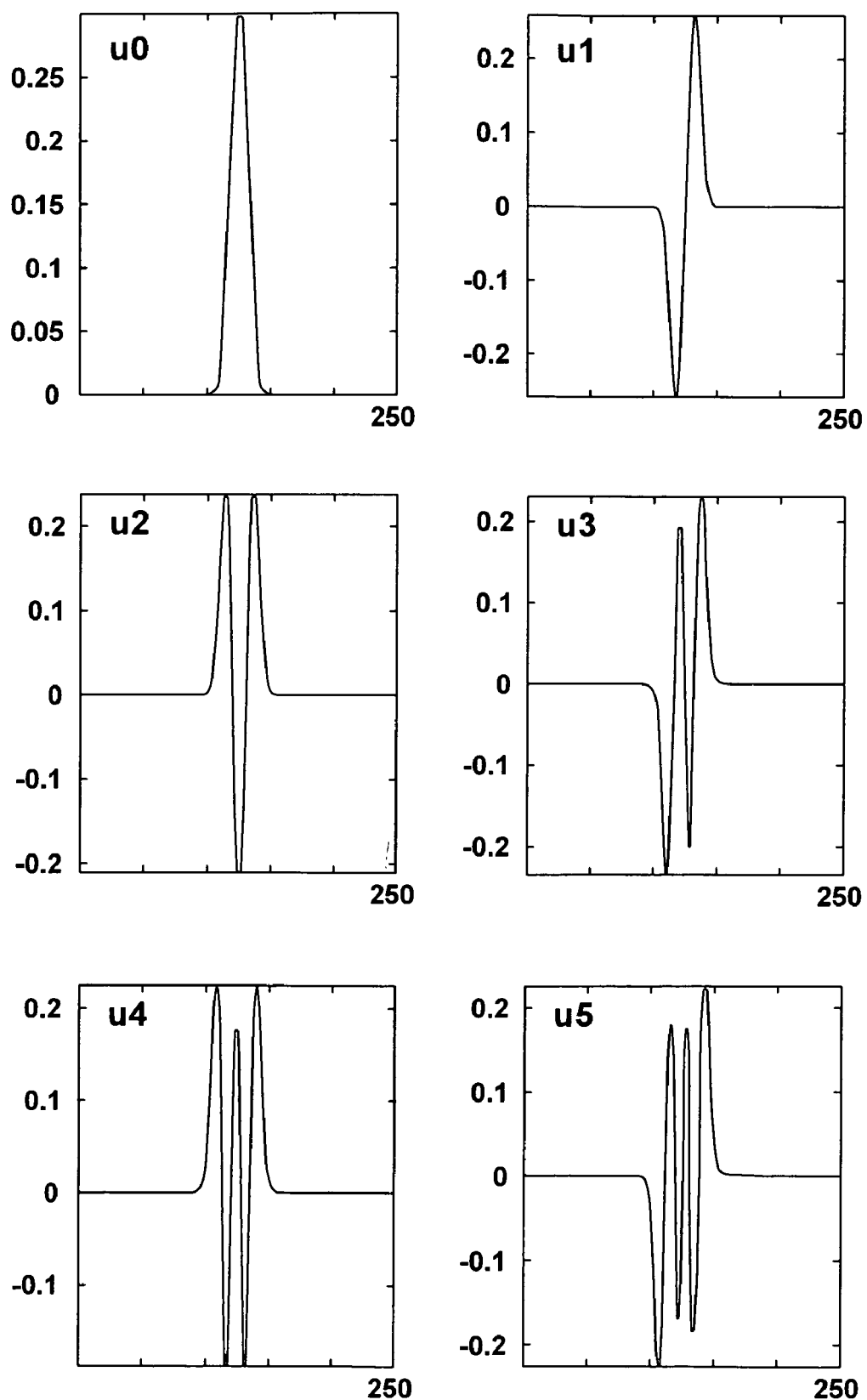
FIG. 1 illustrates the first six Hermite functions $h_{k,\sigma}$ for k=0, 1, . . . , 5 for the $\sigma$=1 undilated case, n=128.

The present invention relates to methods and systems for the use of dilated discrete Hermite functions to expand measured signals using a computationally efficient technique. These digital Hermite functions form the basis for the new discrete Hermite transform which provides information about the shape of the signals, such as that in the BCG artifact in an EEG or in an ECG interval, though the new discrete Hermite transform may be applied to any signal corrupted by noise. As used herein, the term "noise" refers to any signal feature that corrupts, distorts or masks, to any degree, a feature of interest. This applies to any signal measurement technique wherein electrical data is gathered from a patient or source and is susceptible to distortion by factors generated either by the patient or by any external source. Noise may include artifacts, abnormalities, additional signals, and other sources that in any way alter the shape features of a notable, or desired, signal. The Hermite transform coefficients generated on a beat by beat basis contain information unique to the shape features of the signal.

In one embodiment, the present invention may relate to an algorithm for BCG artifact removal making use of the dilated discrete Hermite transform to model the BCG accurately, followed by subtraction from the underlying EEG on a beat by beat basis to give an artifact free signal.

In another embodiment, the present invention may alternatively relate to methods and systems for evaluating abnormalities in electrocardiograms (ECGs), including abnormalities associated with cardiac ischemia, including an automated system and method for interpreting any abnormalities present in an electrocardiogram (ECG), including those abnormalities associated with cardiac ischemia.

In each application, the data signal was refined and/or made more usable so that the diagnostic procedures associated with the data can be quick and accurate. The computational efficiency of the DDHF makes these applications feasible for real-time implementation, unlike the continuous case. As used herein, the term "real-time" means completing the analysis and/or delivering the result of diagnosis without a period of latency so that medical emergency situations can be handled at ease.

The discrete Hermite functions utilized by the present invention are generated as explained below. It is noted that the present invention is not limited to just the digital Hermite functions and/or the method detailed below that is used to generate discrete Hermite functions. The present invention encompasses the entire spectrum of general diagnostic and real-time applications possible with these sets of digital Hermite functions, as applied to any type of electrical signal generated by biomedical diagnostic techniques.

Basic Properties of the Discrete Hermite Transform

The continuous Hermite transform is an integral transform that is well-known in signal processing. Poularikas A. D. (1999), The Handbook of Formulas and Tables for Signal Processing, CRC Press (Chapter 22). According to the invention, a discrete Hermite transform is adapted to digital signals, so that for a digital signal of given length n, there is a complete basis of digital $h_k$ signals for $0 \leq k \leq n-1$ that have properties analogous to the continuous case. For example, the set is mutually orthogonal, satisfies the condition that $F_c k_k = j^k h_k$ (where $F_c$ is the centered Fourier matrix), and each digital function in the set has the basic shape of the correspondingly-indexed continuous Hermite function. Further, each digital basis function $h_k$ is even or odd depending on whether the value of k is even or odd, and the index k still counts the number of zero-crossings of the signal.

This set can be generated in a computationally efficient manner as the set of eigenvectors of a symmetric tridiagonal matrix, which assures their mutual orthogonality, and which is not possible to obtain by simply sampling the continuous signals. An advantage of the tridiagonal matrix T is that it is sparse, and its eigenvectors can be computed efficiently. Because of its symmetries, it can be completely described by its main diagonal, $$x(k) = -2\cos\left(\frac{\pi}{\sigma^2}\right)\sin\left(\frac{\pi k}{n\sigma^2}\sin\left(\frac{\pi}{n\sigma^2}((n-1)-k)\right)\right) \quad (1)$$

for $0 \leq k \leq n-1$, and one of the off-diagonals $$y(k) = \sin\left(\frac{\pi k}{n\sigma^2}\right)\sin\left(\frac{\pi}{n\sigma^2}(n-k)\right) \quad (2)$$

for $1 \leq k \leq n-1$. The symmetries apparent in these formulas can be used to make the computation even faster. The resulting matrix with $h_k$ functions as columns is orthogonal, so the inverse transform simply involves the transpose.

Similar to the continuous function case, these digital Hermite basis functions are non-zero primarily near the center of the interval of definition. The "initial" digital function $h_o$ has the shape of the Gaussian function.

As a special feature, the discrete Hermite transform allows the choice of a dilation parameter $\sigma$ that controls the width of the entire set of digital basis functions. This parameter $\sigma \geq 1$ is related to the standard deviation of the initial Gaussian, but the complete set of digital functions is dilated by that same amount, while still retaining orthonormality. A digital Hermite basis function carries information about its frequency content, since it is essentially its own Fourier transform (subject to appropriate circular translation). In the following, choosing the value of the dilation parameter is of significance, because an appropriate value allows the transform to envelop the entire portion of the signal generated by noise, for example, in an EEG the BCG artifact, with a relatively small number of terms.

Discrete Dilated Hermite Functions as Approximations to Continuous Hermite Functions With the tridiagonal matrix T defined as above, next one should turn to the approximating properties of its eigenvectors. Suppose that $\Psi_k(t)$ for $k \geq 0$ are the continuous Hermite functions, defined by Equation (3) below.

$$\Psi_k(t) = \frac{1}{\sqrt{2^k k! \sqrt{\pi}}} H_k(t) e^{-t^2/2} \quad (3)$$

where $H_k(t)$ are the Hermite polynomials. The polynomials can be calculated recursively by $H_0(t)=1$, $H_1(t)=t$ and $H_k(t)=2tH_{k-1}(t)-2(k-1)H_{k-2}(t)$ for $k \geq 2$.

As noted above, the eigenvectors of T may be ordered based on the size of the corresponding eigenvalue. Let $h_k$ be the kth eigenvector of T, for k=0, 1, ..., n-1 and for dilation parameter $\sigma$, ordered so that k=0 indexes the eigenvector corresponding to the largest eigenvalue, k=1 indexes the eigenvector corresponding to the next largest eigenvalue, etc. With this ordering of eigenvectors, the index of the eigenvector matches the index of the continuous Hermite function that it approximates. The foregoing assumes the $h_{k,\sigma}$ to be normalized, as is the standard for software packages that produce eigenvectors.

Let $T_{n,\sigma}$ be the set of n equally-spaced real numbers that is centered about 0 and whose adjacent points are separated by $$\frac{\Delta t}{\sigma}$$

for a dilation parameter $\sigma$, with $\Delta t = \sqrt{2\pi/n}$ The set can simply be symbolized by J, for the special undilated case when $\sigma=1$. This set of points is the set of sampling points at which the dilated discrete Hermite functions will approximate the continuous Hermite functions. This set of points is shown below in Equation (4)

$$T_{n,\sigma} = \{m\Delta t/\sigma\} \quad (4)$$

for $$m = -\frac{n-1}{2}, -\frac{n-1}{2}+1, \ldots, \frac{n-1}{2}.$$

That is, the first element of $T_{n,\sigma}$ is $$-\frac{n-1}{2}\frac{\Delta t}{\sigma}$$

and the last element is $$\frac{n-1}{2}\frac{\Delta t}{\sigma}$$

The dilated discrete Hermite functions $h_{k,\sigma}$ approximate the continuous Hermite functions $\Psi_k(t)$ at the points $T_{n,\sigma}$ from Equation (4). Symbolically, $h_{k,\sigma}[m] \approx \Psi_k(t_m)$, where $t_m$, is the mth term in the ordered set $J_n$. That is, the kth eigenvector $h_{k,\sigma}$ approximates the similarly-indexed classical continuous Hermite function sampled at the set of points $T_{n,\sigma}$ (and normed to 1). Note that the vector on the right side of this equation must also be of unit norm to satisfy this approximation, as the eigenvectors are already normalized in this way. It should be noted that the error in the approximation increases as the index k increases. For small values of k the error is very small, and increases gradually as k increases. One of the advantages of the set of dilated discrete Hermite functions is that each set, for fixed $\sigma$ is an orthonormal basis because this set consists of eigenvectors of a symmetric, tridiagonal matrix.

Discrete Hermite Expansions of Signals

The discrete Hermite transform of an input signal of length n is simply the result of an expansion of the digital signal in the orthonormal basis $h_k$, $0 \leq k \leq n-1$ described above. The discrete Hermite transform of the signal gives a set of transform values which corresponds to the inner product of the input signal with the basis functions, just as the discrete Fourier transform is an inner product with discrete complex exponentials. After selection of the dilation parameter σ, the n×n matrix whose columns are the $h_k$'s described above serves as the matrix for the discrete transform. The even-odd symmetry of the digital functions allows for a relatively fast computation of the transform (and inverse transform). The fast transform, according to the invention, makes use of the even-odd symmetries of the $h_k$ vectors to halve the number of multiplications required in the standard dot product.

In contrast to the Fourier transform that reveals frequency content, the discrete Hermite transform primarily reveals shape content of the underlying signal. For example, if the discrete Hermite transform of an input x is $x^H = [2, 3, -1, 0, \ldots, 0]$ the function is $x = 2h_0 + 3h_1 - k_2$.

Given a digital signal (i.e. vector) x of length n, the discrete Hermite expansion (Equation (5)) of x is simply an expansion of an n-dimensional digital signal in a particular orthonormal basis. This expansion has the form shown in Equation (5) below.

$$x = \sum_{k=0}^{n-1} c_{k,\sigma} h_{k,\sigma} \quad (5)$$

with coefficients $$C_{k,\sigma} = (X, h_{k,\sigma}) \quad (6)$$

given by standard inner products of the input signal with the discrete dilated Hermite functions.

Digital signals that are even or odd are especially easy to represent in an expansion of dilated discrete Hermite functions. Similar to the continuous Hermite functions, $h_{k,\sigma}$ is even or odd, depending on whether k is even or odd, $k=0, 1, \ldots, n-1$. This property is valid for any value of the dilation parameter σ. For example, if input x is even, only even-indexed $h_{k,\sigma}$ will have non-zero coefficients. For a more general signal, it is important to emphasize that any digital signal has a representation as shown in Equation (5) since this set of discrete Hermite functions provides an orthonormal basis. There are, however, two parameters to determine in order that the expansion have as few non-zero coefficients as possible; the two parameters available for determining the expansion are (i) the center and (ii) the dilation parameter value σ.

For a digital signal obtained from electrophysiological measurements, there is often a zero-crossing of the signal near the middle of the finite time support, and that would provide the center point for the expansion. The dilation parameter σ is a new possibility for discrete Hermite functions. For example, in applications to ECG signals, the center point is determined by a standard QRS detection algorithm and the value of σ will be chosen so that feature points in the ECG signal match those of a similar $h_{k,\sigma}$ vector.

Figure 2:
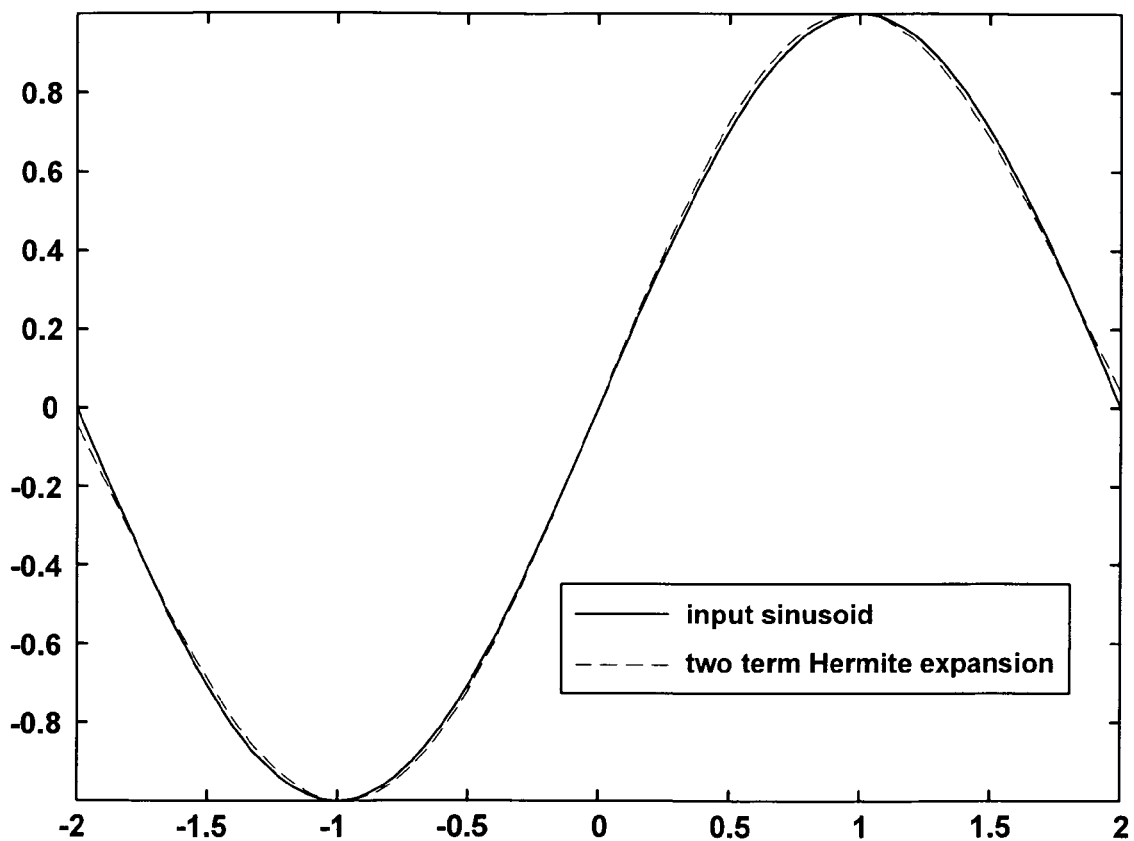
FIG. 2 illustrates an approximation of sinusoid by an expansion with just two discrete Hermite functions.

As a simple example of an Hermite expansion, consider the expansion of one cycle of the sinusoid $\sin(\pi t/2)$ over $-2 \leq t \leq 2$. This sinusoid is an odd function. The even-indexed coefficients, $h_{0,\sigma}$ and $h_{2,\sigma}$ are zero since the inner product of an odd function and an even function is zero. If only two terms in the Hermite expansion Equation (5) are used, the first two non-zero coefficients in the discrete Hermite expansion correspond to $h_{2,\sigma}$ and $h_{3,\sigma}$. The resulting two-term expansion with σ=1 approximates this sinusoid with relative error averaging only 3.9%. Also, the first two non-zero coefficients in the expansion account for 99% of the coefficient energy (see FIG. 2).

Applications to ECG Signals

While not limited thereto, and merely to provide one skilled in the art with a working example, the present invention has been applied to ECGs in order to approximate and compress the ECG signals. In one embodiment, the method of the present invention is appropriate for the QRS complex of an ECG signal. The R pulse of the complex is a dominant feature, and methods have already been established to detect this complex within the ECG signal. If one of these methods is employed, the QRS complex may be centered with the maximum point of the R segment at the origin of an interval. The resulting QRS complex has the general shape similar to some of the low-indexed Hermite functions, such as $h_2$ and $h_4$ in FIG. 1. This suggests that a good approximation of Equation (5) for the QRS complex of the ECG signal may be accomplished using relatively few discrete Hermite functions.

One of the difficulties in using continuous Hermite functions to approximate the QRS complex of an ECG signal is that a modern recording is both digital and finite in length, whereas the classical Hermite functions are continuous and are defined for all values of t. If those Hermite functions are simply sampled and the resulting vectors used for an expansion, those vectors are not orthogonal. Coefficients in such an expansion cannot be found by simple inner products as in Equation (6). However, the discrete dilated Hermite functions have the advantage in representing digital signals that they are an orthonormal set of signals where the expansion of the signal may be found easily and efficiently.

An advantage of this method in representing the QRS complex of an ECG signal is that the discrete dilated Hermite functions are localized. The $h_k$ are concentrated near the origin for small k indices, and expand outward with greater width as the index k increases. In particular, if one considers $h_k^2$ as a probability distribution, then it can be shown that the standard deviation is approximately $$\sigma \sqrt{\frac{2k-1}{4\pi}},$$

which increases with index k. If the signal to be modeled is concentrated near the origin, this property of digital Hermite functions makes it possible for just a few of the first discrete Hermite functions in the expansion shown in Equation (5) to give an excellent approximation.

For applications to ECG signals, the first set of examples assume that the QRS complex is about 200 ms in duration (which is conservative) and that 100 ms of zero values are added on the right and the left in order to center and isolate the QRS complex. Signals used here for the examples, as given in the following figures, were obtained from the following database—E. Traasdahl's ECG database as sponsored by the Signal Processing Information Base (SPIB), (see http://spib.rice.edu/spib/data/signals/medical/ecg_man.html). The database assumed a sampling rate of 1 kHz, so that signals used here have length n=400 samples: 200 samples of QRS complex data, and 100 zero samples at the beginning and end. The data were high-pass filtered to remove the dc component.

Figure 3:
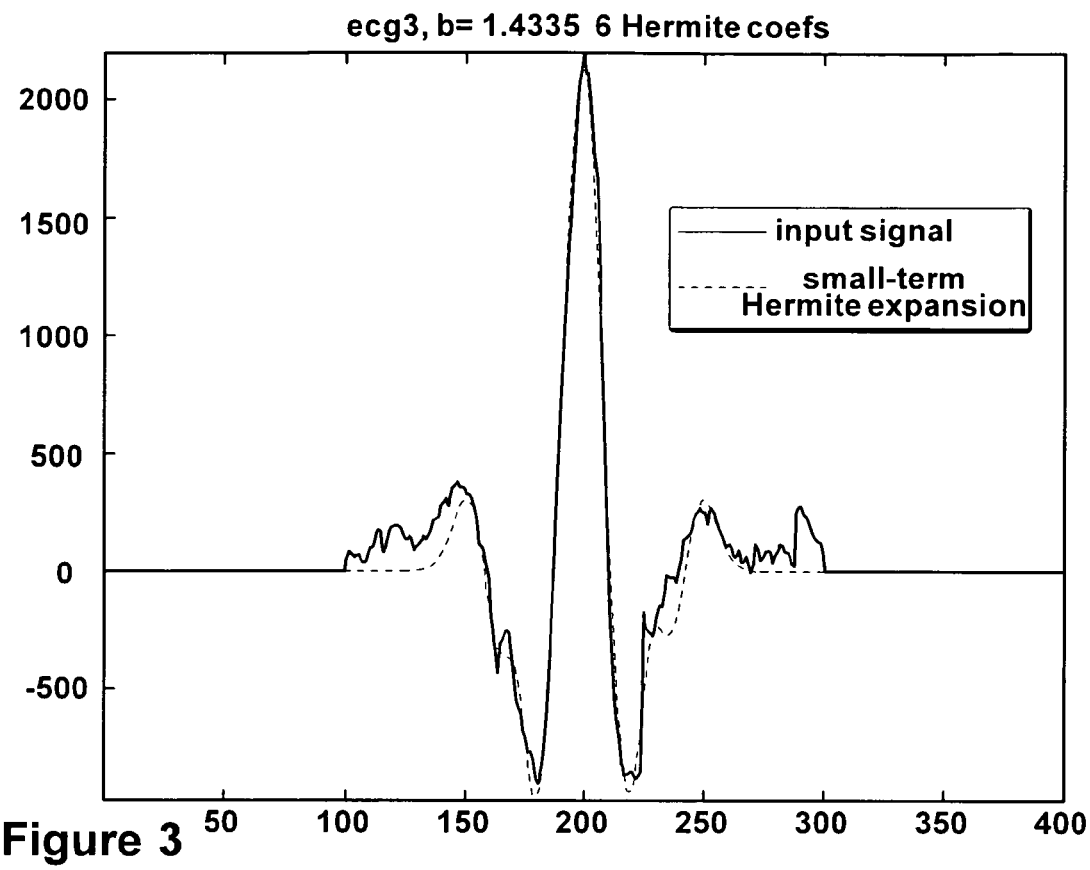
FIG. 3 is an illustration of an ECG signal approximation with six digital Hermite functions, σ=1.43.
Figure 4:
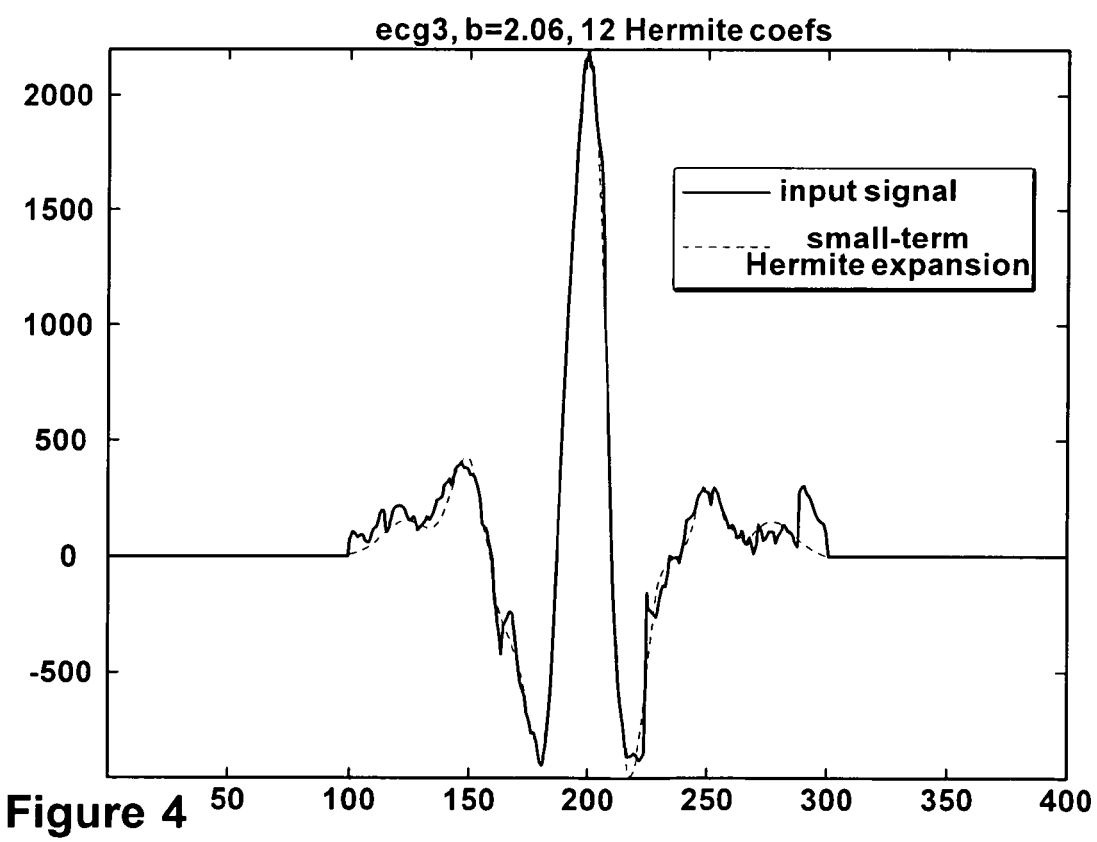
FIG. 4 is an illustration of the ECG signal of FIG. 3 approximated using 12 digital Hermite functions and a larger scale parameter σ=2.06.
Figure 5:
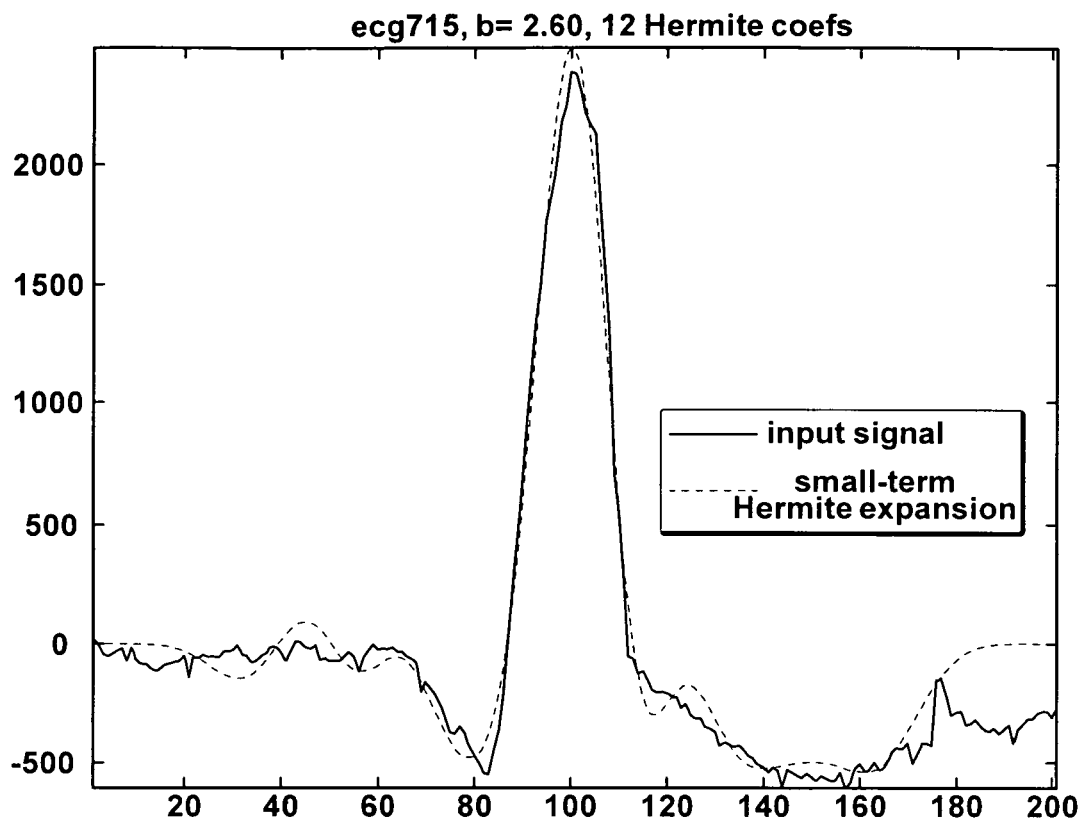
FIG. 5 is an illustration of an ECG signal approximation using 12 discrete Hermite functions, σ=2.60.
Figure 6:
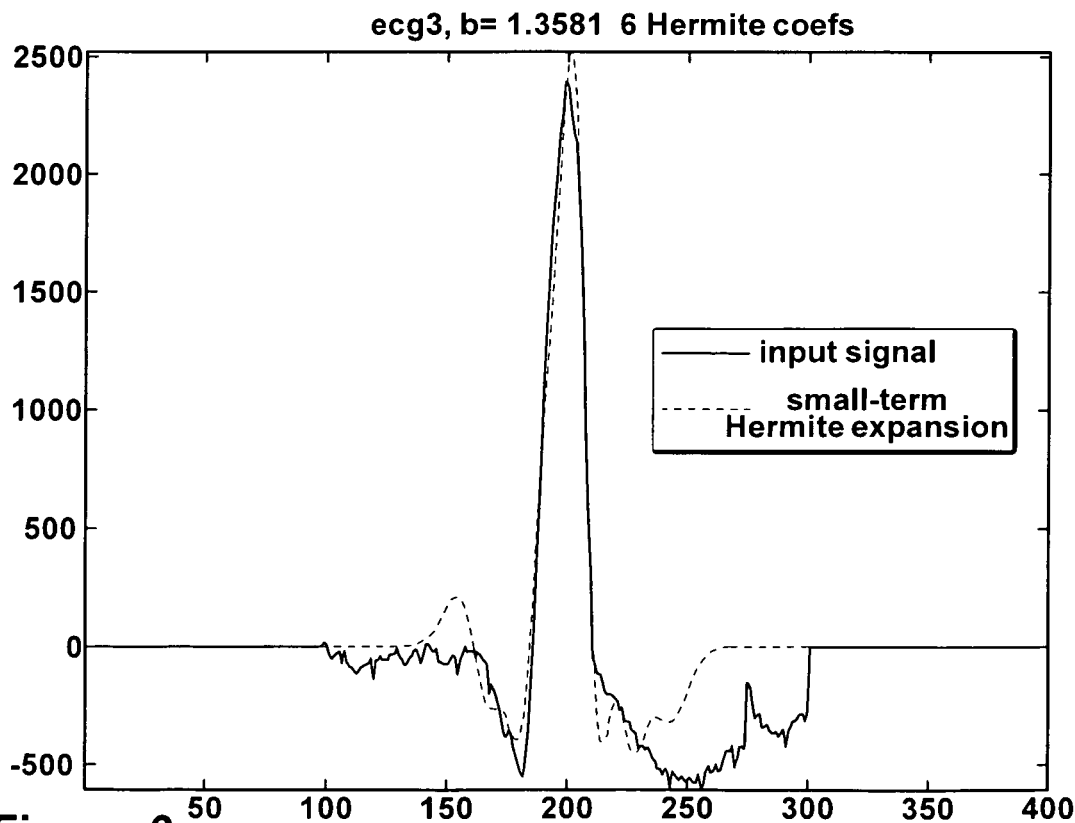
FIG. 6 is an illustration of the ECG signal of FIG. 5 approximated using six digital Hermite functions and a smaller dilation parameter σ=1.36.
Figure 7:
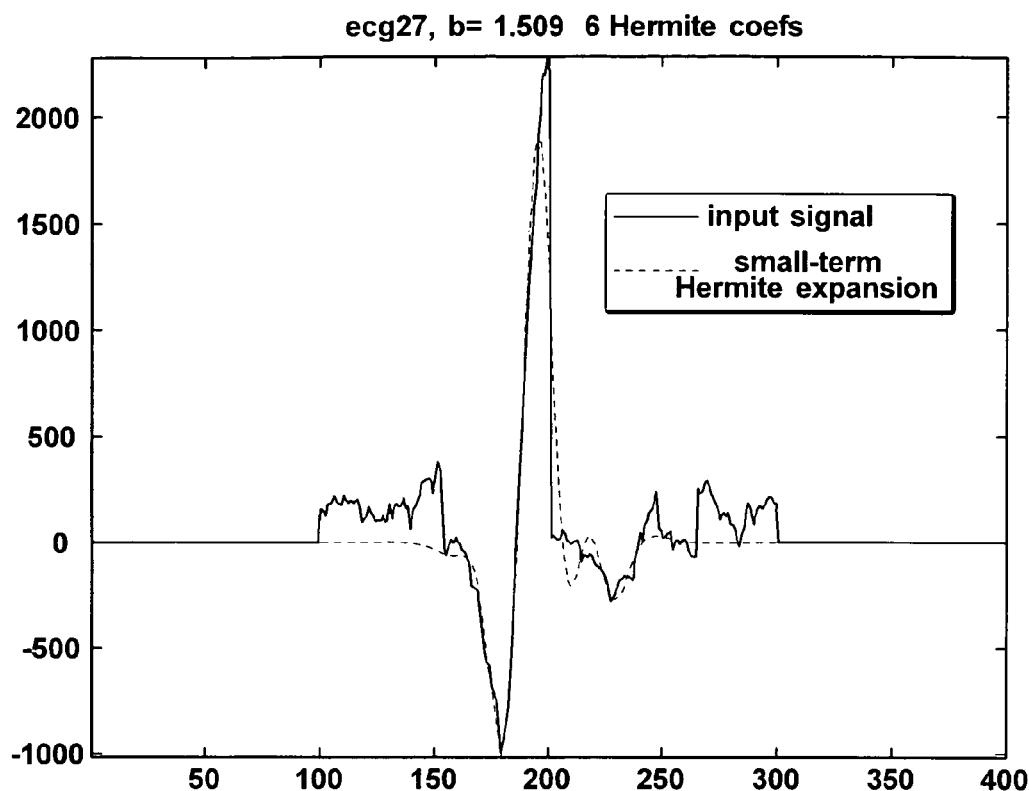
FIG. 7 is an illustration of an ECG signal approximation using six discrete Hermite functions, σ=1.51.
Figure 8:
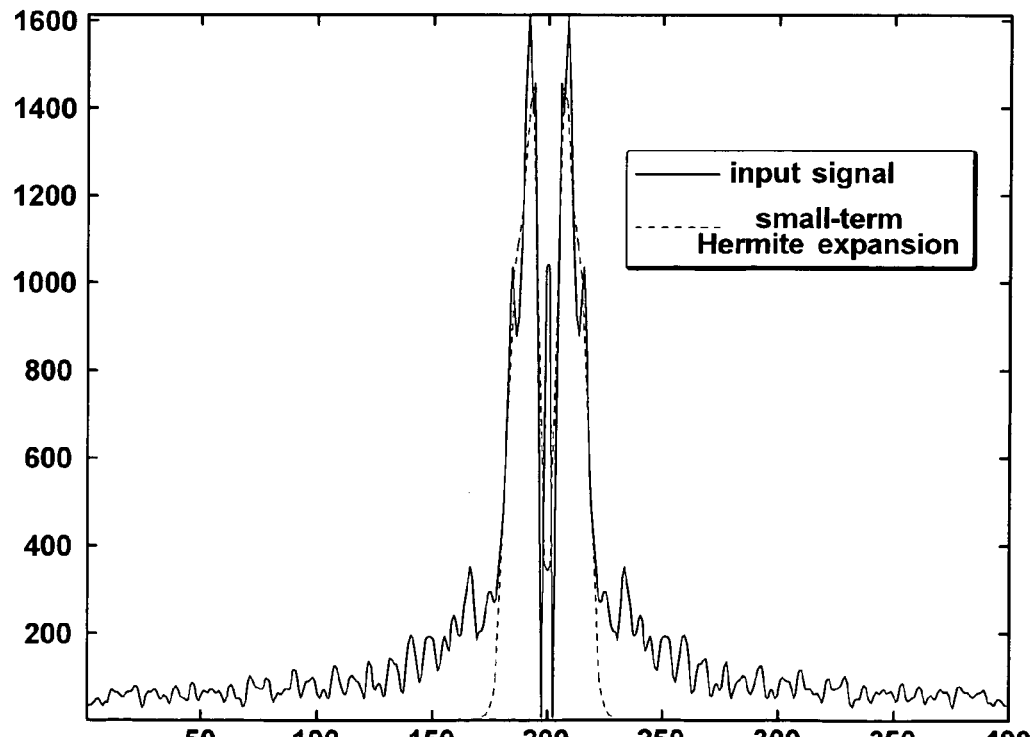
FIG. 8 is an illustration of a centered Fourier transform ECG signal from FIG. 9 using six digital Hermite functions.

An expansion of a signal x in terms of discrete dilated Hermite functions as in Equation (5) includes the choice of the dilation parameter value σ. Since the methods of the present invention involve fast computations, the choice of σ is also based on a quick computation. As noted earlier, the general shape of the QRS complex is similar to $h_2$, although $h_2$ is symmetric and the QRS complex is generally not symmetric. If the positive-valued bumps outside of the QRS complex are included, then the shape is often similar to $h_4$. The criterion for choosing σ that is favored, in one embodiment, by the present invention is based on $h_2$. In this embodiment, the minimum value of $h_2$ is matched with the minimum of the signal (Q or S) that is closer to the origin. Since $h_2$ is actually a vector, the choice of σ is based on a discrete analysis instead of a continuous one. The actual equation used is shown below in Equation (7).

$$\sigma = \frac{\Delta t \cdot \min(xleft, xright)}{\sqrt{5/2} + 0.08} \quad (7)$$

where 'xleft' and 'xright' are the integer-valued horizontal distances from the origin to the input signal's minimum to the left and right of the origin, respectively. With this choice of dilation parameter σ, signals such as those in FIGS. 3 and 7 are well-approximated using only six digital Hermite functions in the expansion of Equation (5). A formula similar to Equation (7) for σ applies for when the match is for $h_4$, and results for those cases are shown in FIGS. 4 and 5, where a very good approximation of the signal is obtained with 12 discrete Hermite functions. Compare FIG. 6 with six digital Hermite functions to FIG. 5 with twelve. If the bowl-shaped S portion of this signal is important for medical evaluations, then the approximation with 12 digital Hermite functions would be necessary. Finally, FIG. 8 shows that the (centered) Fourier transform of the discrete Hermite approximation has basically filtered the noisy transform of the ECG signal.

Further Expansion of ECG Signals

Figure 9A:
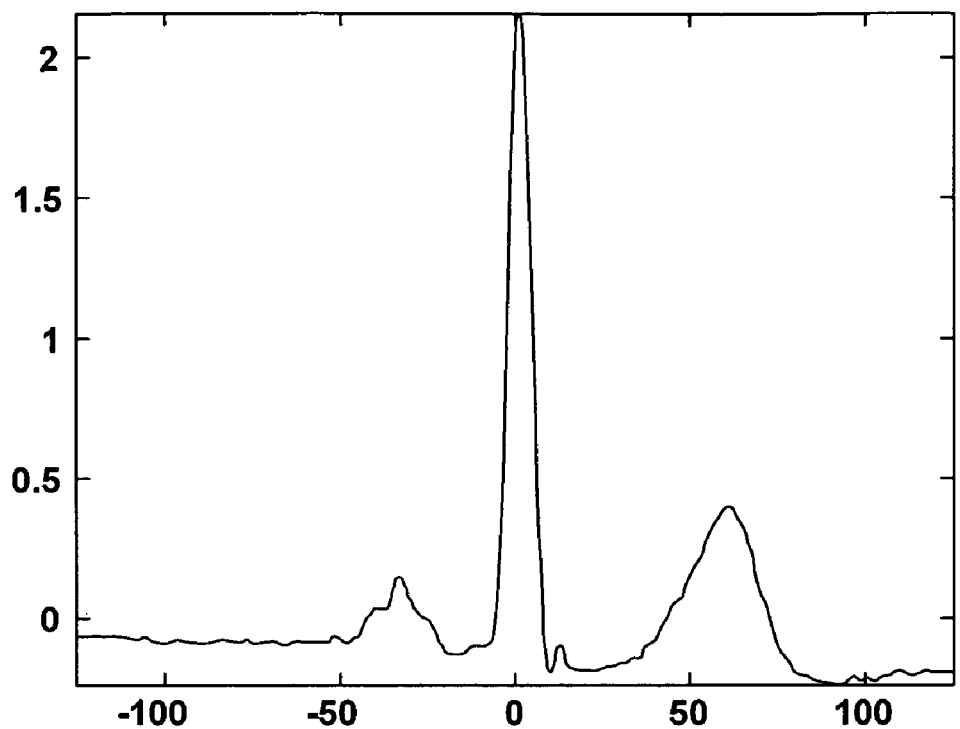
FIG. 9(a) is an original electrocardiogram.
Figure 9B:
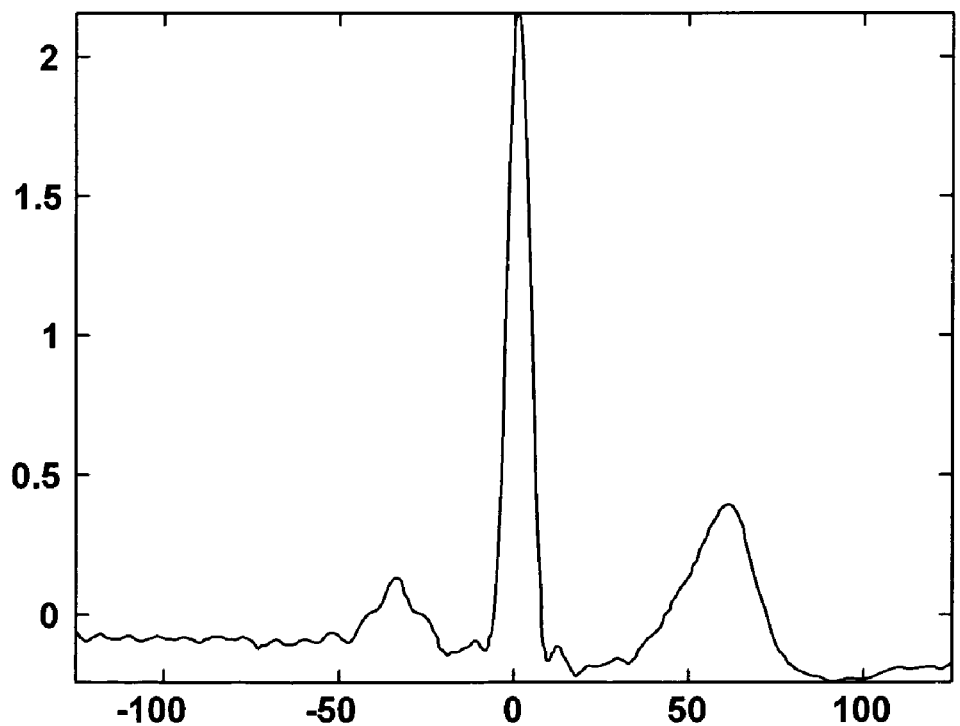
FIG. 9(b) is a reconstruction of the electrocardiogram of FIG. 9(a) using 50 discrete Hermite functions.

In light of the above, individual ECG complexes were centered at their R-peaks and the corresponding discrete Hermite transform was calculated, using the principles noted earlier. A dilation parameter of σ=1 was used. The performance of the calculated Hermite coefficients in representing the EGG was calculated using the Percentage RMS Difference (PRD) error, given by $$PRD = \sqrt{\Sigma_i (x_i - y_i)^2 / \Sigma_i (x_i - \bar{x})^2} \quad (8)$$

where $x_i$ is the original ECG signal, $y_i$ is the Hermite representation and $\bar{x}$ is the mean of the signal. In this embodiment, the first 50 digital Hermite coefficients are sufficient for reconstructing the ECG with an acceptable PRD, although the present invention is not limited to just this embodiment. FIGS. 9(*a*) and (*b*) show a comparison of an original ECG signal and its reconstruction using the first 50 Hermite coefficients.

Figure 10:
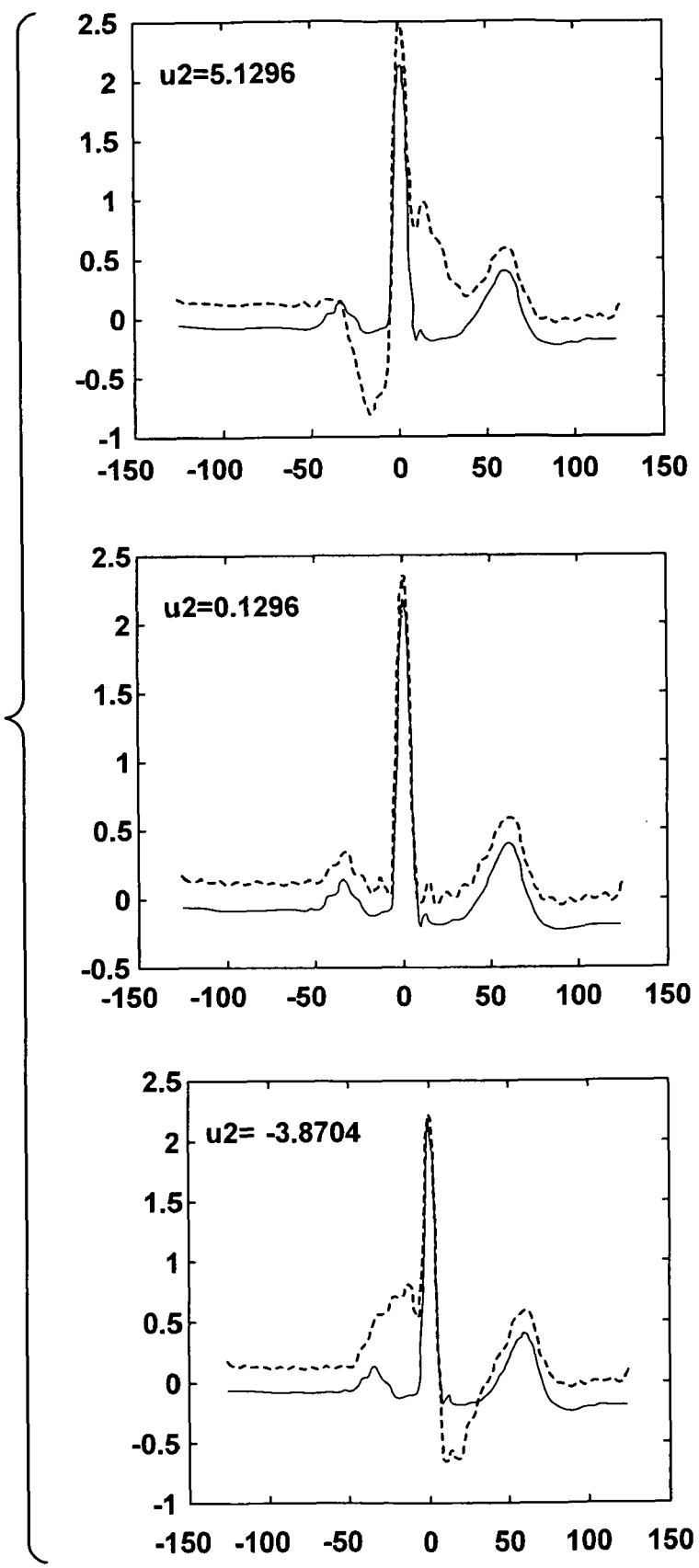
FIG. 10 illustrates the adaptation of the second digital Hermite function to the shape of an electrocardiogram (ECG) (to enable visualization of the discrete Hermite expansion, a small offset is present in FIG. 10).

Changes in ECG features are reflected as variations in the values of the Hermite coefficients. As an example, FIG. 10 illustrates the contribution of the second digital Hermite function towards the reconstruction process, for coefficient values 5.1296, 0.1296 and −3.8704. As can be seen from FIG. 10, the second discrete Hermite function with a large positive coefficient value fits ischemic features like deep Q wave and an ST segment elevation in the ECG. As the value approaches near zero, it fits a normal ECG. For a large negative value, it fits an ischemic ST depression feature. All of the 50 coefficient values, considered together, are a measure of the shape of the ECG and can be used as a tool for identification of ischemic features. However, in the absence of a clearly identifiable relationship between the coefficients and specific ECG features, a Neural Network based method was adopted.

For long term ECG monitoring applications, an automated method for segmentation, the discrete Hermite expansion followed by classification was developed. One such embodiment of the present invention is outlined in FIG. 11. Using a QRS detection algorithm, long term ECG signals were scanned for R-peak locations. This was used to automatically segment the ECG, with each ECG complex centered at its R-peak, and having a window size equivalent to the corresponding R-R interval. The discrete Hermite transform corresponding to the individual ECG complexes was calculated as shown earlier.

The first 50 coefficients were the input to a trained Neural Network classifier. The network outputs were the presence or absence of ST segment changes, T wave changes and ischemia, which for this type of measurement technique can be considered noise in accord with the invention.

Five Neural Networks were trained with the 50 Hermite coefficients as inputs. The networks had three layers with different number of hidden layer neurons. The 2 outputs of the network were presence/absence of ST segment changes and presence/absence of T-wave inversion. A committee of Neural Networks was used, since individual network results might vary in borderline ischemic cases. The majority decision of the committee of trained neural networks was used in arriving at the final classification.

Preliminary Training of a Committee of Neural Networks: The training data set consisted of 236 ECG complexes, containing both ischemic or noise signals as well as normal ECG signals The ECG signals were taken from the MIT-BIH database, predominantly from European ST-T database and long term ST-T database. The ischemic ECG signals were chosen based on 2 features: (1) an elevated/depressed ST segment and (2) an inverted T wave. All possible combinations of these two features were presented to the network. MATLAB Neural Network Toolbox was used for the training. The Conjugate gradient back propagation algorithm was used to train the Neural Networks.

Adaptive Training: In addition to the training, the network was retrained with a few samples of normal ECG cycle from each long term record that was used for testing. This was performed to show the network a feel of the normal ST segment and T-wave features from the particular long term ECG and to find out if the network was able to detect any changes in the ST and T wave features that occurred during ischemic episodes.

Figure 11:
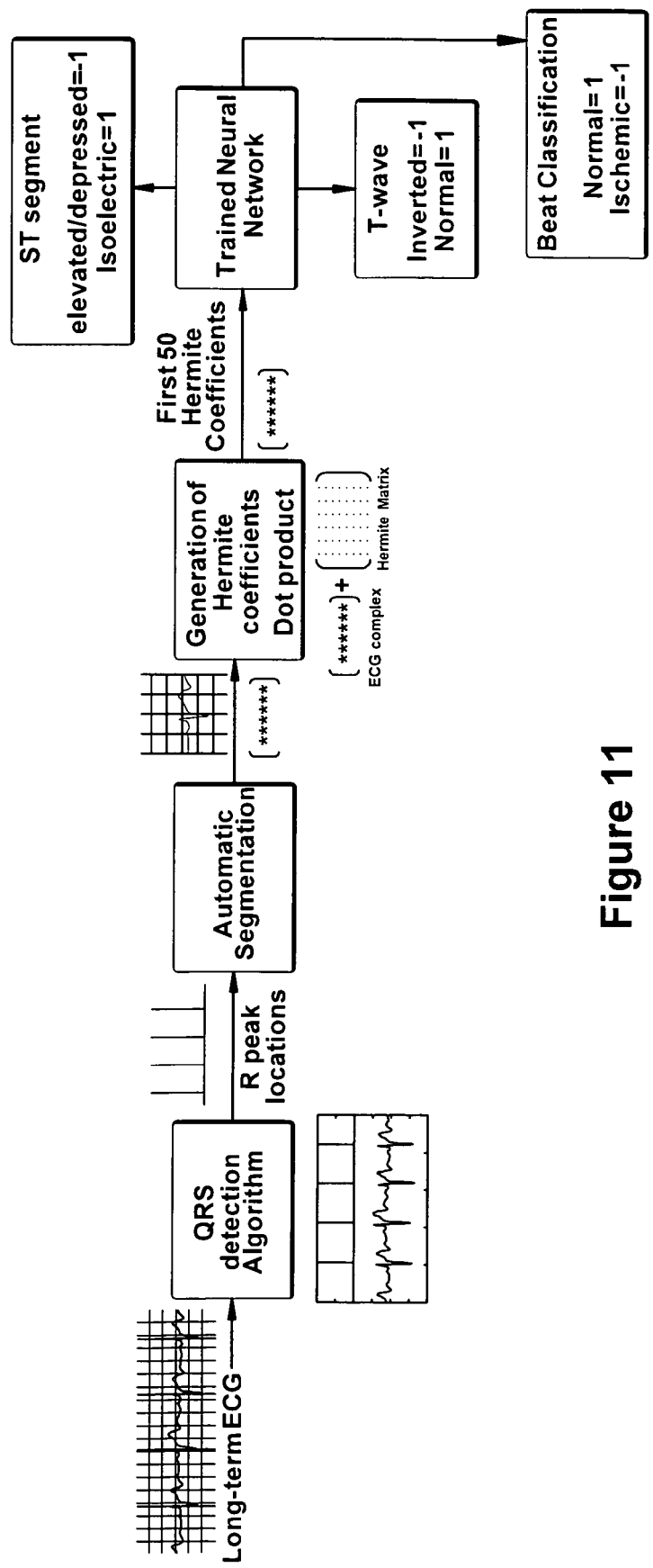
FIG. 11 is a block diagram of a system, according to one embodiment of the present invention, that is designed to monitor for ischemia in long term electrocardiogram signals.

Testing: Twenty-four long-term ECG records from the European ST-T database were used to test the validity of the above method of the present invention, in simulated real-time conditions The ECG records were continuously scanned for R-peak locations, by the methods described previously, and sets of 50 discrete Hermite coefficients were simultaneously generated. The trained Neural Networks were used for beat-to-beat classification of the ECG, vis-à-vis ST segment and T wave changes (FIG. 11). A majority decision of the Committee of Neural Networks was used for arriving at the final decision.

Figure 12A:
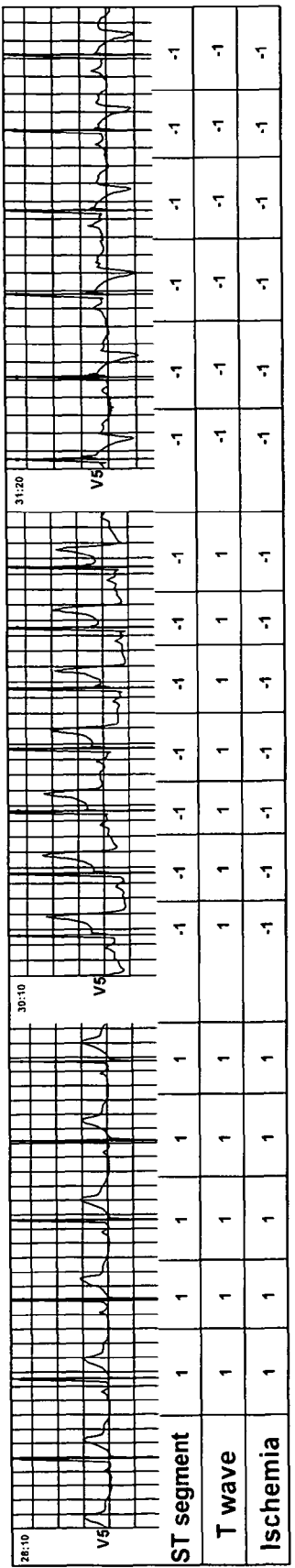
FIG. 12(a) is a illustration of various segments of ECG signals from record e0111 of the European ST-T database and the corresponding Neural Network output generated by the ischemia monitoring system/method of the present invention.
Figure 12B:
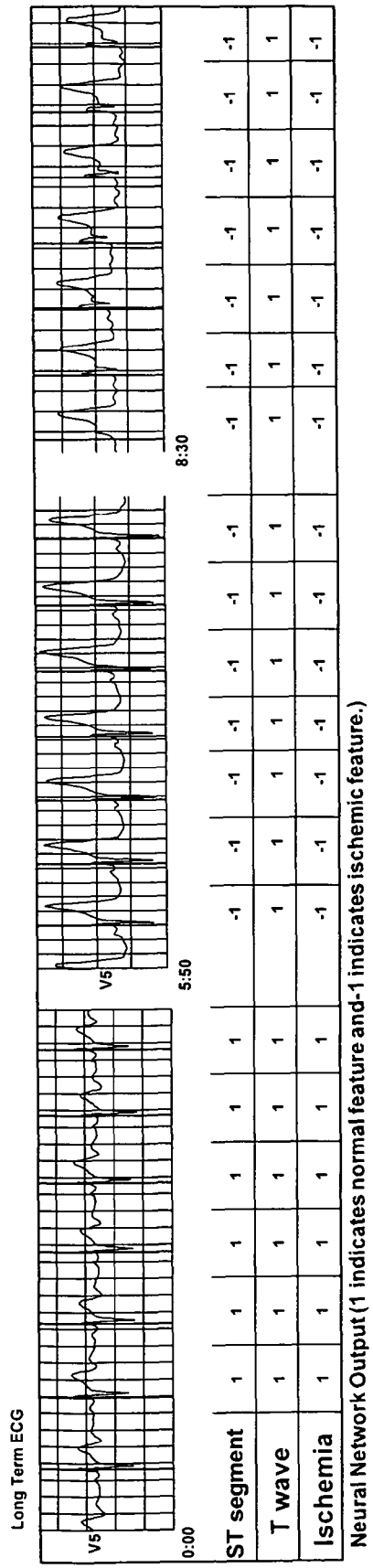
FIG. 12(b) is a illustration of various segments of ECG signals from record e0603 of the European ST-T database and the corresponding Neural Network output generated by the ischemia monitoring system/method of the present invention.

Results: A total of 1918 beats were used to test the trained networks. The results are tabulated in Table 1. For ST segment changes, a sensitivity of 97.2% and a specificity of 98.6% were observed. For T-wave inversion, a sensitivity of 98.6% and a specificity of 93.3% were observed. Overall, for ischemic episode detection, a sensitivity of 98% and a specificity of 97.3% were observed (Table 2). FIGS. 12(*a*) and (*b*)

show the output of the committee of Neural Networks, in classifying a long term ECG record on a beat to beat basis.

TABLE 1

Results for Beat Classification

| | Ischemic Episode in ECG (Number of samples) | | | |
|---|---|---|---|---|
| | ST Segment Change | | T Wave Change | |
| Test Result | Present | Absent | Present | Absent |
| Positive | 1166 | 10 | 1179 | 48 |
| Negative | 33 | 709 | 20 | 671 |
| Total | 1199 | 719 | 1199 | 719 |

ST: Sensitivity = 1166/1199 (97.2%) and Specificity = 709/719 (98.6%)
T: Sensitivity = 709/719 (98.6%) and Specificity = 671/719 (93.3%)

TABLE 2

Results for Episode Classification

| | Ischemia (Number of samples) | |
|---|---|---|
| Test Result | Present | Absent |
| Positive | 1175 | 19 |
| Negative | 24 | 700 |
| Total | 1199 | 719 |

Sensitivity = 1175/1199 (98%) and Specificity = 700/719 (97.3%)

Comparison with Other Methods: Table 3 shows a comparison of sensitivity and specificity of some commonly used ischemia detection methods with the digital Hermite transform based approach according to the invention. As can be seen from Table 3, the method of the present invention has enhanced sensitivity and specificity better than most others considered in detecting ischemic episodes.

TABLE 3

Comparison Chart

| System Category | Sensitivity | Specificity |
|---|---|---|
| Digital Signal Analysis [1], [2] | 85.20 | — |
| Digital Signal Analysis [3] | 95.80 | 90.00 |
| Digital Signal Analysis [4] | 95.00 | 100.00 |
| Rule Based (ST Episodes) [5] | 92.02 | — |
| Rule Based (T Episodes) [5] | 91.09 | — |
| Fuzzy Logic [6] | 81.00 | — |
| Artificial Neural Networks [7] | 79.32 | 75.19 |
| Artificial Neural Networks [8] | 89.62 | 89.65 |
| Present Invention's Method | 98.00 | 97.30 |

[1] Technique based on Jager F, Mark R. G, Moody G. B, et al, "Analysis of Transient ST Segment Changes during Ambulatory ECG Monitoring using Karhunen-Loeve Transform", *Proc. IEEE Comput. Cardiol.*, pp. 691-694, 1992.
[2] Technique based on Jager F, Moody G, Mark R, "Detection of Transient ST Segment Episodes during Ambulatory ECG Monitoring", *Comput. Biomed Res.*, No. 31, pp. 305-322, 1998.
[3] Technique based on Baldilini F, Merri M, Benhorin J, et al. "Beat to Beat Quantification and Analysis of ST Ddisplacement from Holter ECGs; A New Approach to Ischemia Detection", *Proc. IEEE Comput. Cardiol.*, pp. 179-182, 1992.
[4] Technique based on Senhadji L, Carrault G, Bellanger J, et al. "Comparing Wavelet Transform for Recognizing Cardiac Pattern", *IEEE Eng. Med. Biol.*, No. 14(2): pp. 161-173, 1995.
[5] Technique based on C. Papaloukas, D. I. Fotiadis, A. Likas, et al. "Use of a Novel Rule Based Expert System in the Detection of Changes in the ST Segment and T Wave in Long Duration ECGs", *J. Electrocardiol.*, No. 35(1), pp. 105-112, 2001.
[6] Technique based on Vila J, Presedo J, Delgado M, et al. "SUTIL: Intelligent Ischemia Monitoring System", *Int J. Med. Inf.*, No. 47(3), pp. 193-214, 1997.
[7] Technique based on Stamkopoulos T, Diamantaras K, Maglaveras N, et al. "CG Analysis Using Nonlinear PCA Neural Networks for Ischemia Beat Detection," *IEEE Trans. Signal. Process*, No. 46(11), pp. 3058-3067, 1998.
[8] Technique based on Maglaveras N, Stamkopoulos T, Diamantaras K, et al. "ECG Pattern Recognition and Classification using Linear Transformations and Neural Networks: A Review", *Int. J. Med. Inf.*, No. 52, pp. 191-208, 1998.

As mentioned above, the present invention is, in one embodiment, directed to a method for the real-time, automated identification of ischemic features from ECG signals. The method of the present invention is very effective in extracting shape features from the ECG signals. The computation of coefficients is simple and fast. The method of the present invention can be implemented for continuous bed side monitoring and offline inspection of ECG in ischemic patients. The results stated herein show an excellent sensitivity, which is crucial in bedside monitoring and screening of long term records.

Applications to EEG-fMRI Signal Processing

In another embodiment of the present invention, the discrete dilated Hermite transform is applied to an EEG. Simultaneous EEG-fMRI data was recorded from three subjects, two of which were healthy and one of which was a stroke patient at the Johns Hopkins University. In all, 65 channels of EEG data were recorded using the Synamps 2 amplifier (Compumedics Neuroscan, TX). The data recorded was pre-processed using EEGLAB, an add-on toolbox of MATLAB, making it compatible to the data in MATLAB and therefore more easily accessible. A finger plethysmograph was used to monitor the blood volume pulse. Using the location of this pulse as a temporal reference, a window was computed which typically contained the BCG artifact, or noise. This windowed data was then bandpass filtered in the range of 3-14 Hz, which is considered to be the range in which the BCG artifact lies. This was done with care not to eliminate the underlying delta band or the frequency baseline changes within the recorded EEG signal and also to be able to model the BCG artifact more accurately.

The discrete Hermite transform of this bandpass filtered windowed data was computed. The first few coefficients, (about 75, or one-twelfth the total length of about 900 samples of the band pass filtered signal) obtained using the forward Hermite transform were retained while the remaining were set to zero. The inverse discrete Hermite transform of this signal was computed using this new set of coefficient values. The reconstructed signal modeled the shape and amplitude features of the BCG artifact. This modeled BCG artifact was then subtracted from the original non-bandpass filtered signal, to obtain the BCG artifact-free EEG signal. This whole process was repeated for every cardiac cycle. To validate the results of the developed algorithm, four different test cases were performed. These included: (i) an EEG signal recorded within the scanner with the BCG artifact embedded; (ii) a normal EEG signal recorded outside the scanner with a known BCG artifact template added; (iii) an EEG signal with spikes; and (iv) an alpha wave recorded with eyes closed and a known BCG template added.

The results of this algorithm for the different test cases performed are as shown in FIGS. 13 through 16.

Results for EEG signal with Embedded BCG Artifact

Figure 13A:
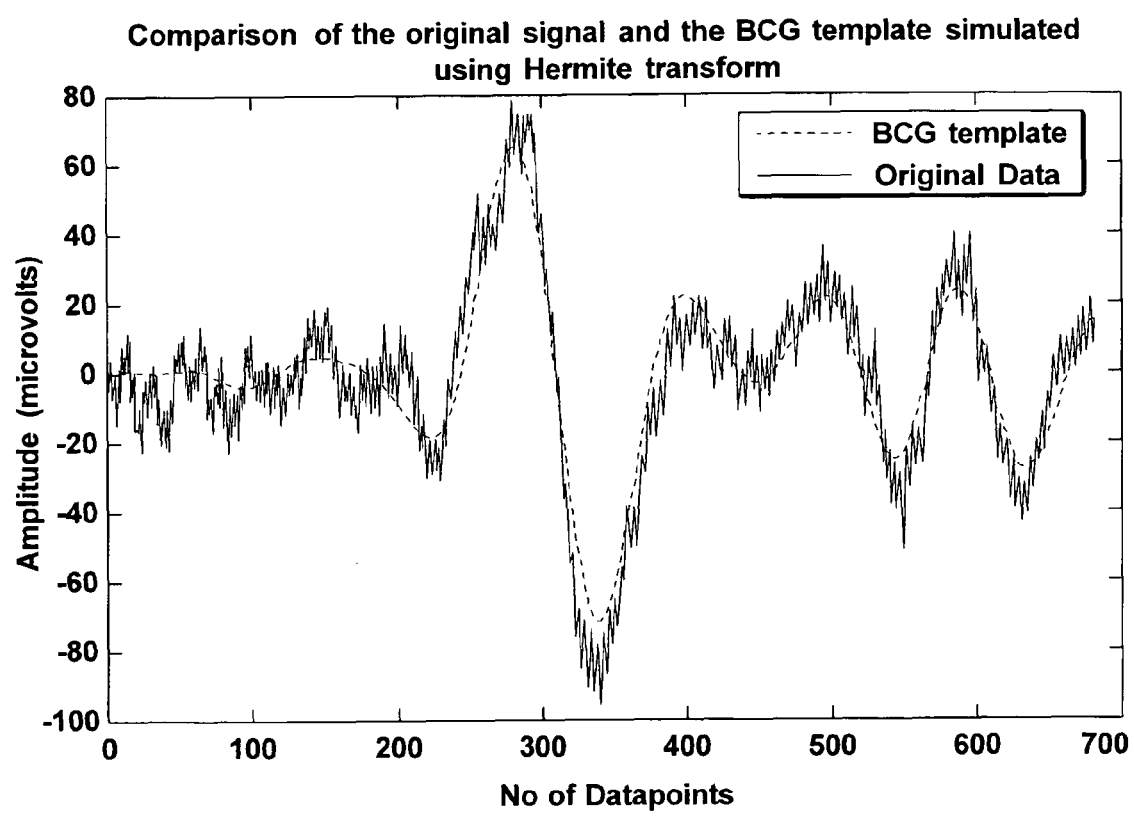
FIG. 13(a) is a model of the BCG template created using discrete Hermite functions as compared to the original signal in accord with the present invention.
Figure 13B:
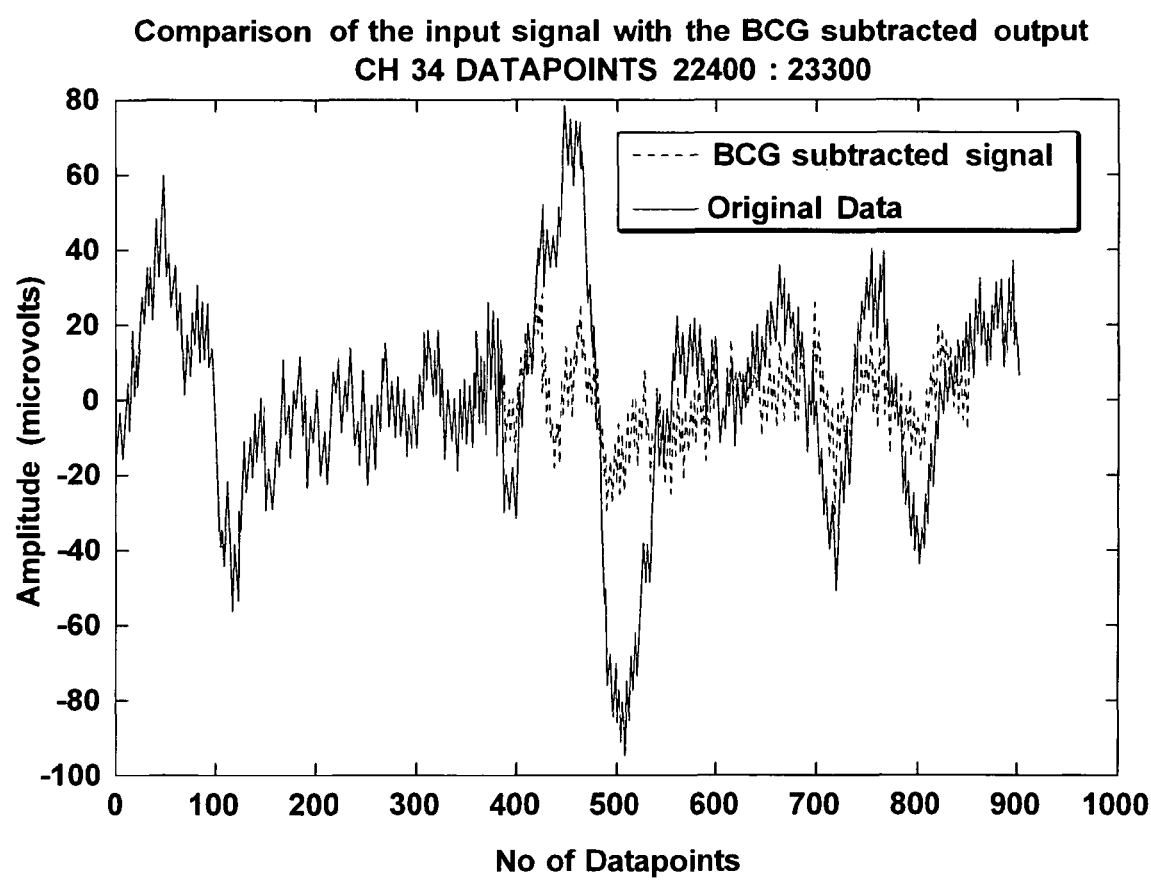
FIG. 13(b) is a comparison of the original and BCG subtracted output of the signals from FIG. 13(a) in accord with the present invention.
Figure 13C:
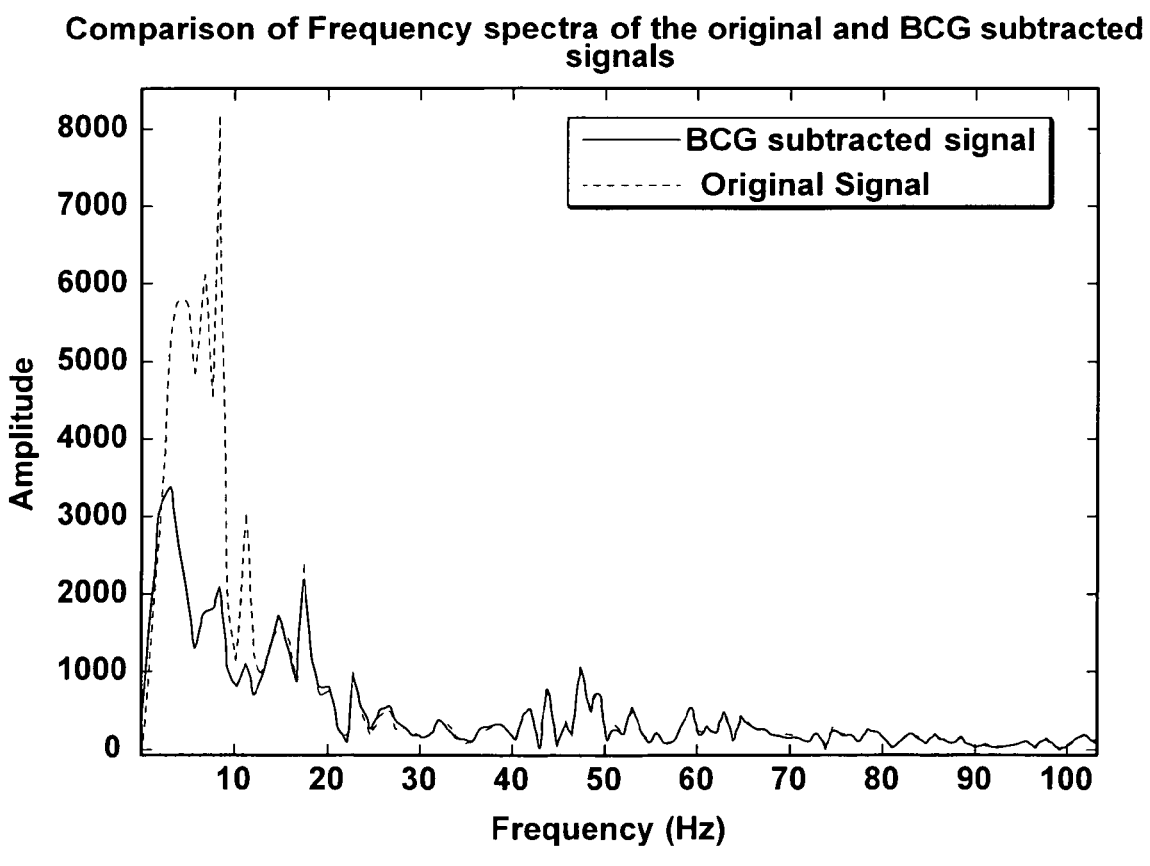
FIG. 13(c) is a comparison of frequency spectra of the original recorded signal with that of the BCG subtracted signal as shown in FIG. 13(a) in accord with the present invention.

For the first test case implemented, an EEG signal recorded from one of the subjects for the $34^{th}$ channel was taken as the input to the algorithm. FIG. 13(a) clearly shows a BCG artifact, or noise, embedded within the recorded EEG signal. It also depicts the simulated BCG artifact obtained using the discrete Hermite transform algorithm. It can be seen that the BCG artifact is well modeled according to the input signal. FIG. 13(b) shows the original input recorded EEG within the scanner and the BCG subtracted signal obtained as the output of the algorithm. FIG. 13(c) shows a plot of comparison of frequency spectra for the original and the BCG subtracted signals. With reference to these FIGS. 13(a)-(c), it is observed that there is a significant reduction in amplitude at the lower frequencies especially in the 3-14 Hz range, without eliminating that entire frequency band. This is crucial, as many important EEG signals like the alpha and mu rhythms have their frequency spectra in this range.

Results for Normal EEG with Known BCG Artifact Template Added

Figure 14A:
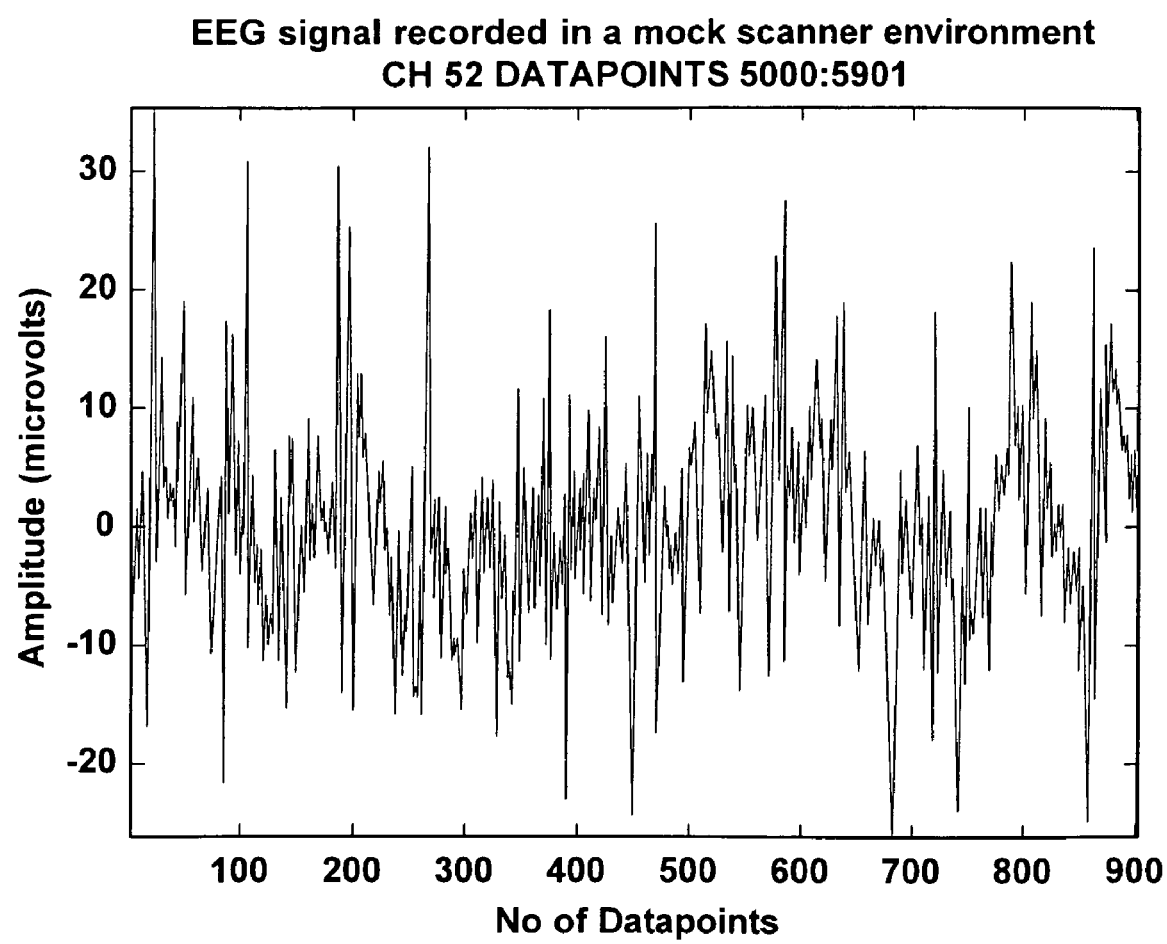
FIG. 14(a) is a plot of an EEG signal recorded in a mock scanner in accord with the present invention.
Figure 14B:
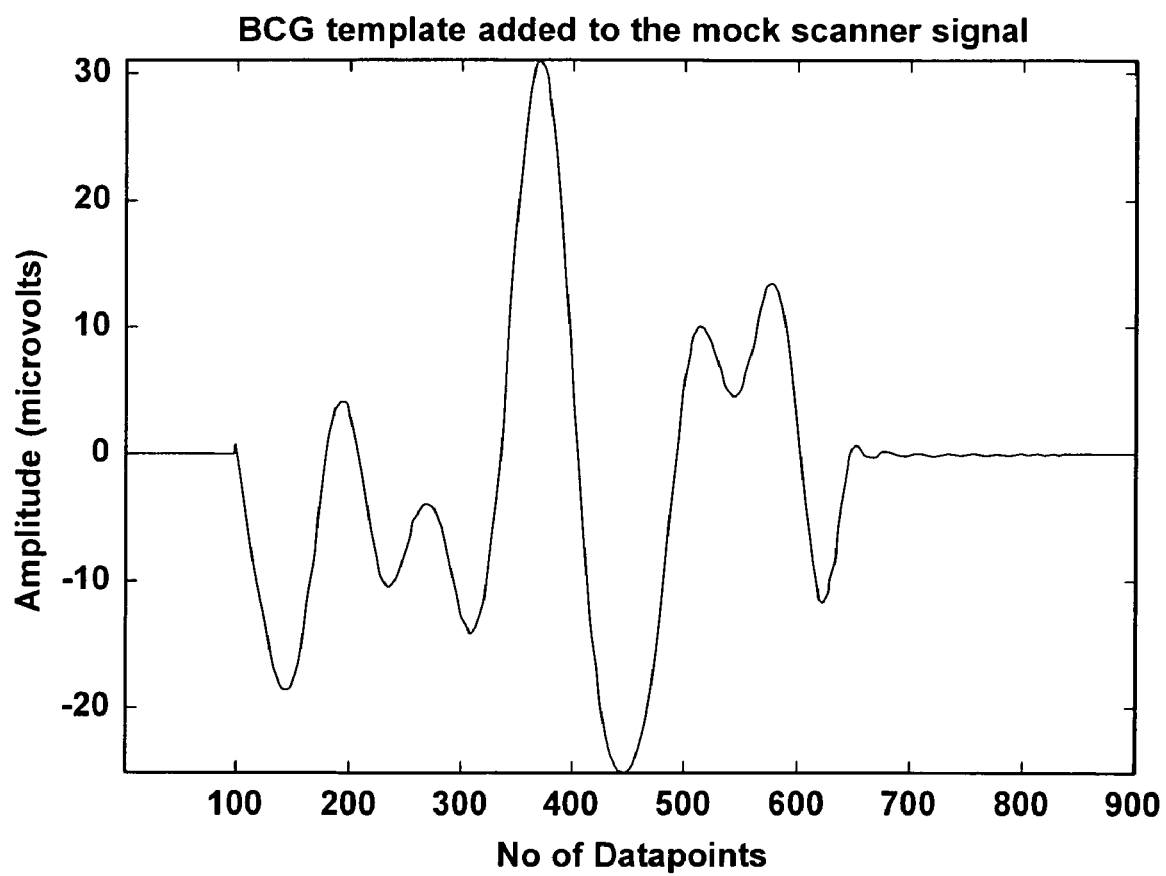
FIG. 14(b) is a BCG template added to the EEG plot shown in FIG. 14(a) in accord with the present invention.
Figure 14C:
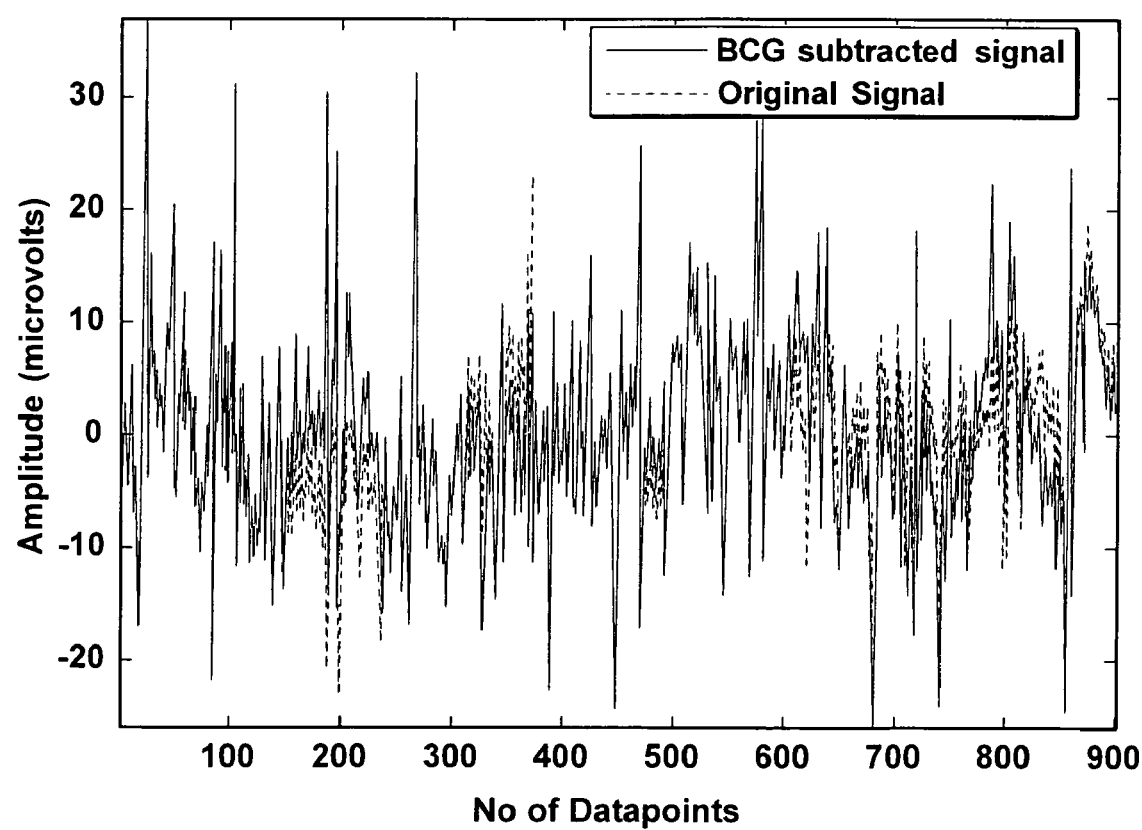
FIG. 14(c) is a comparison of the outputs of the original and the BCG subtracted signals for FIG. 14(a) in accord with the present invention.
Figure 14D:
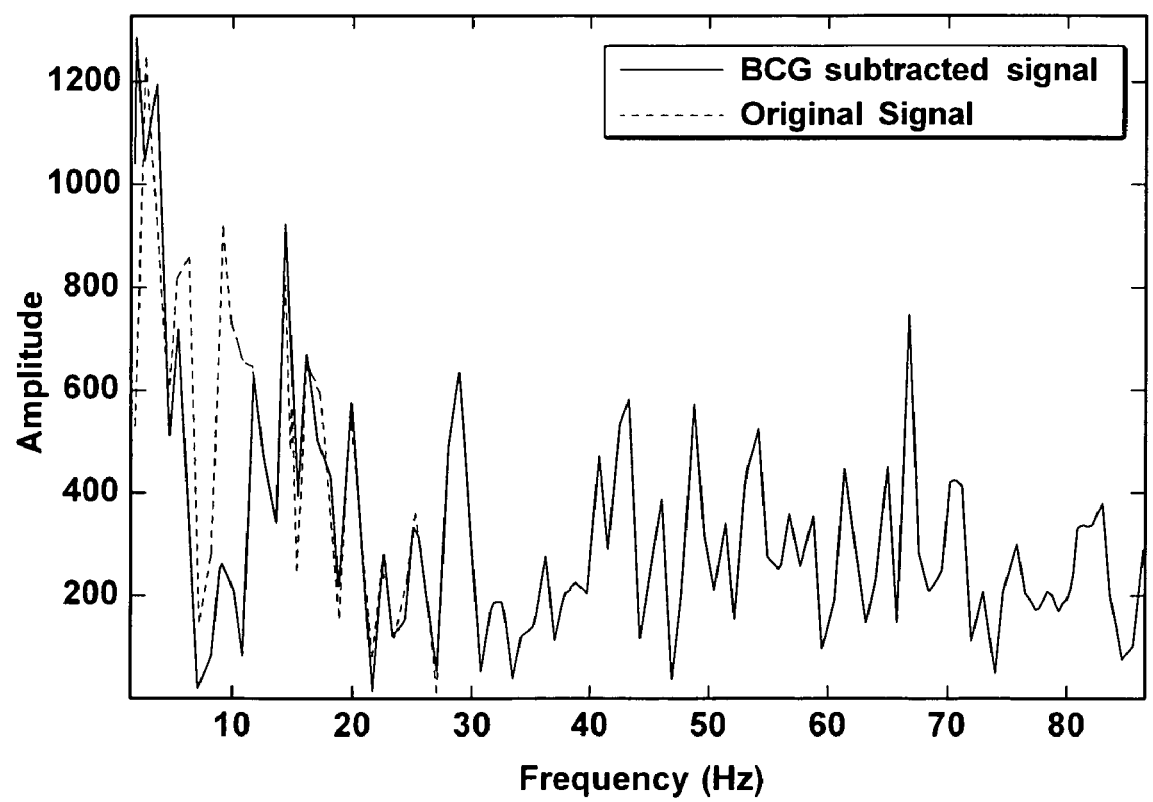
FIG. 14(d) is a comparison of frequency spectra of the original and BCG subtracted signals relating to FIG. 14(a) and in accord with the present invention.

For the second test of an EEG with a known BCG template added, the algorithm was able to successfully eliminate the BCG noise only. For this purpose, an EEG recorded within the mock scanner for a subject was taken as an input. A known BCG template created using the Hermite algorithm was added to this signal. This EEG-BCG mixture was given as an input to the algorithm and the output was compared to the original signal. FIG. 14(a) shows the normal EEG signal recorded in a mock scanner while FIG. 14(b) shows the BCG template added to it. FIGS. 14(c) and 14(d) show the comparison of the outputs and frequency spectra respectively. From FIG. 14(c), it can be seen that, the input and the output after BCG subtraction obtained from the algorithm match quite well, though there are small shifts in the baseline at a few points. To determine if the difference between these two signals is significant, a Wilcoxon's signed rank test was performed on this data. The 'p' value obtained on doing this test was 0.1874 (p>0.05) suggesting that there exists no significant difference between the input and the output signal. Furthermore, from FIG. 14(d), it is observed that the frequency spectrum of the original mock scanner signal and the BCG subtracted signal closely correspond to one another. This shows that the algorithm is effective in removing only the ballistocardiogram and not any signals of interest.

Results for EEG Signals with a Spike

Figure 15A:
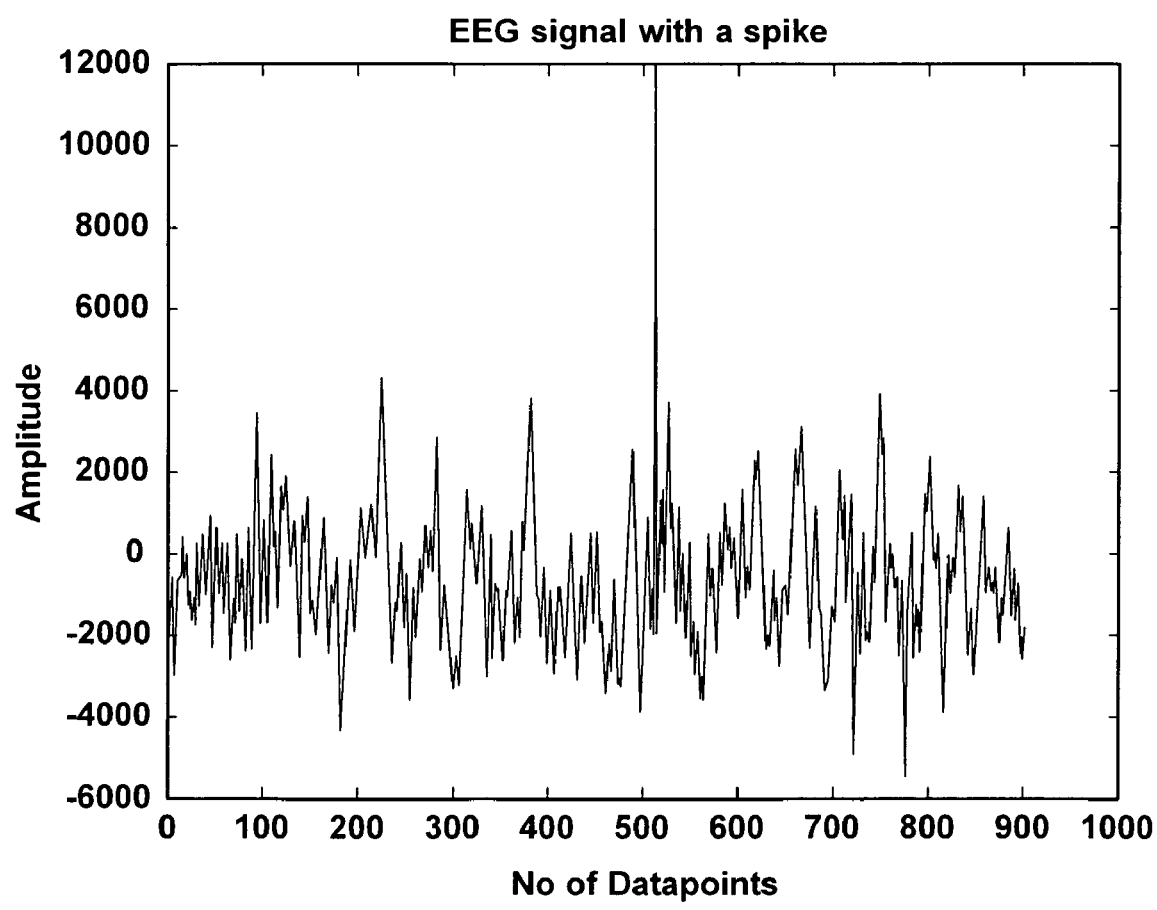
FIG. 15(a) is a plot of an EEG signal with a spike according to the present invention.
Figure 15B:
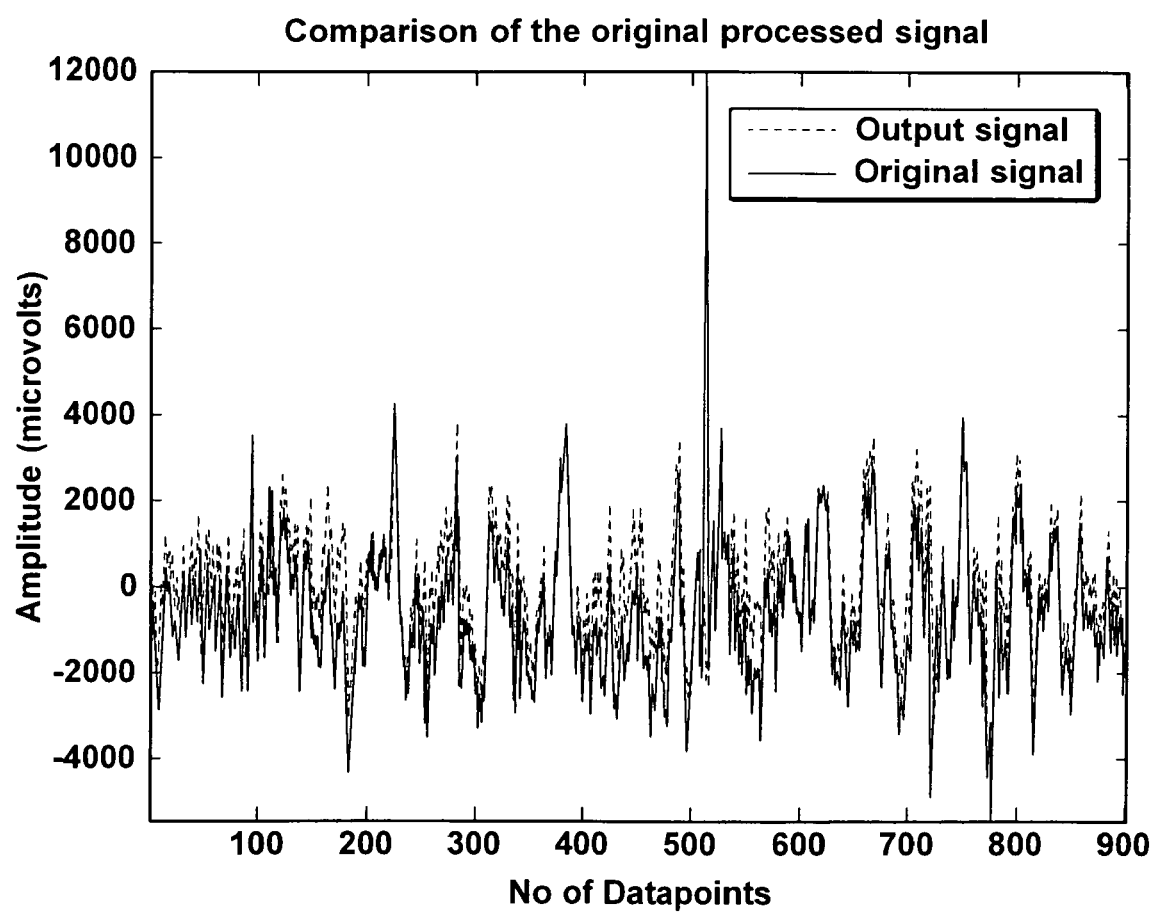
FIG. 15(b) is a plot of outputs of the original and processed signals of the EEG of FIG. 15(a) in accord with the present invention.
Figure 15C:
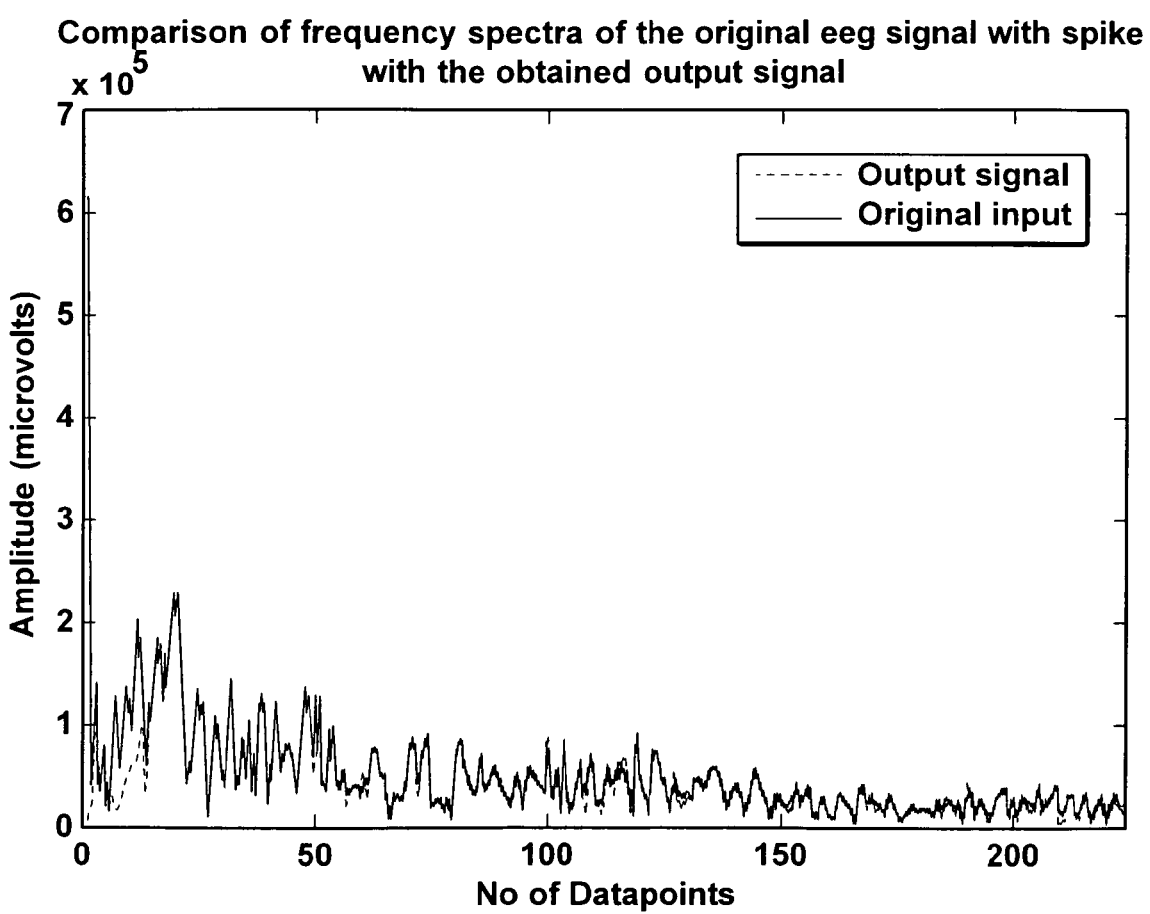
FIG. 15(c) is a plot of frequency spectra of the original and processed signals of the EEG plot of FIG. 15(a) in accord with the present invention.

The third test case simulated used EEG signals with a spike. This was to test if the algorithm is able to identify and maintain the spikes (e.g. epileptic spikes) within the signal intact in the final output. The signal used for this test did not contain a BCG artifact. FIG. 15(a) shows the original signal with a spike and FIG. 15(b) shows the comparison of the input and the output signal. It is observed that the spike in the original signal and the output signal is at the same location and that they have the same amplitude as well. FIG. 15(c) shows the frequency comparison plot of the input and output signal. It can be seen from FIG. 15(c) that some low frequency components (4-12 Hz) are suppressed. This is attributed to the fact that, since the original signal did not contain any BCG artifact and still was passed through the BCG artifact removal algorithm, a few low frequency components were eliminated. However, this test case was conducted mainly to check if the EEG spike within the signal is retained, which was supported.

Results for Alpha Wave with Known BCG Template Added

Figure 16A:
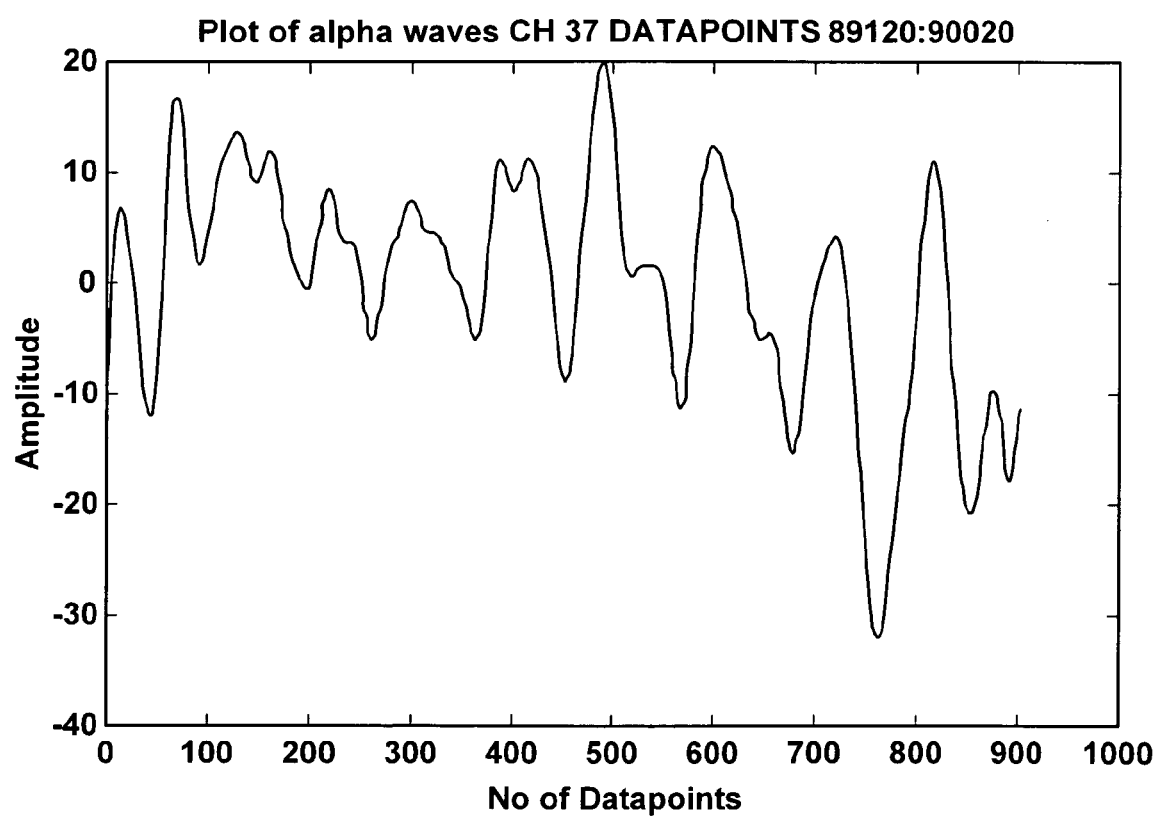
FIG. 16(a) is an EEG recording with no fMRI (Alpha waves) in accord with the present invention.
Figure 16B:
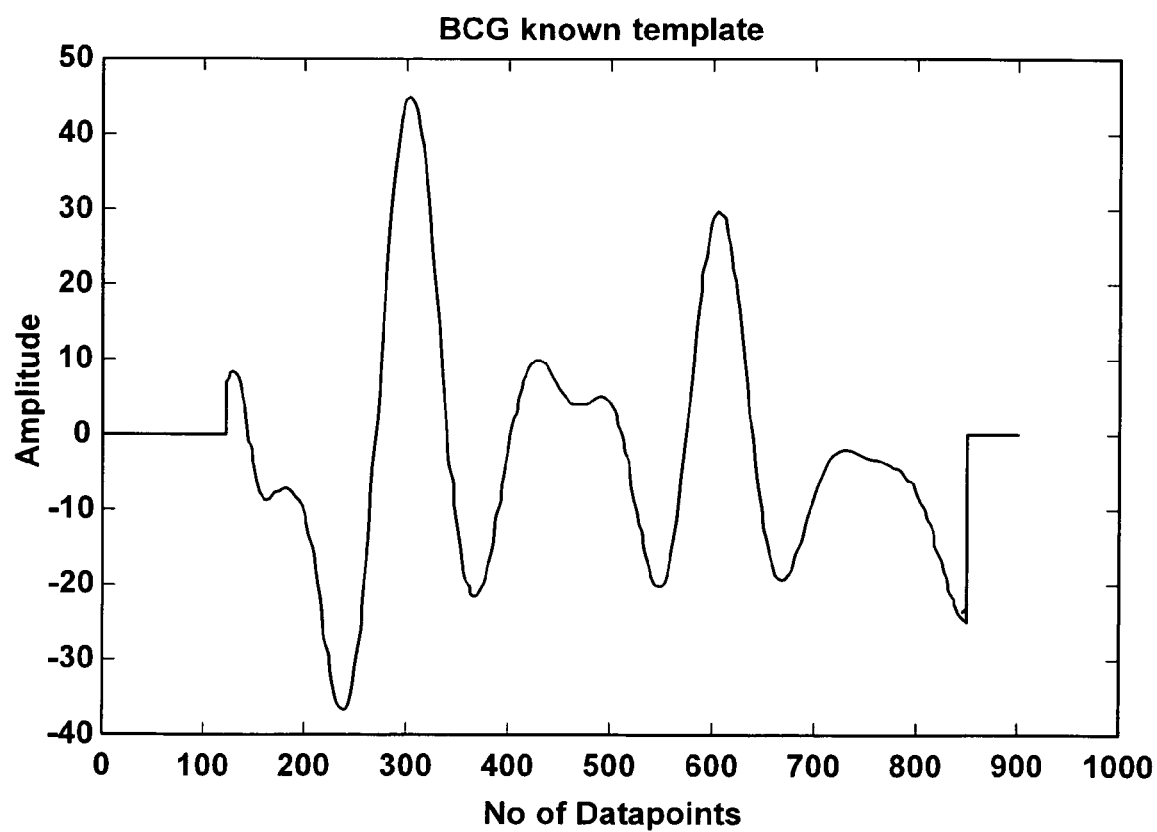
FIG. 16(b) is a BCG template added to the signals shown in FIG. 16(a) in accord with the present invention.
Figure 16C:
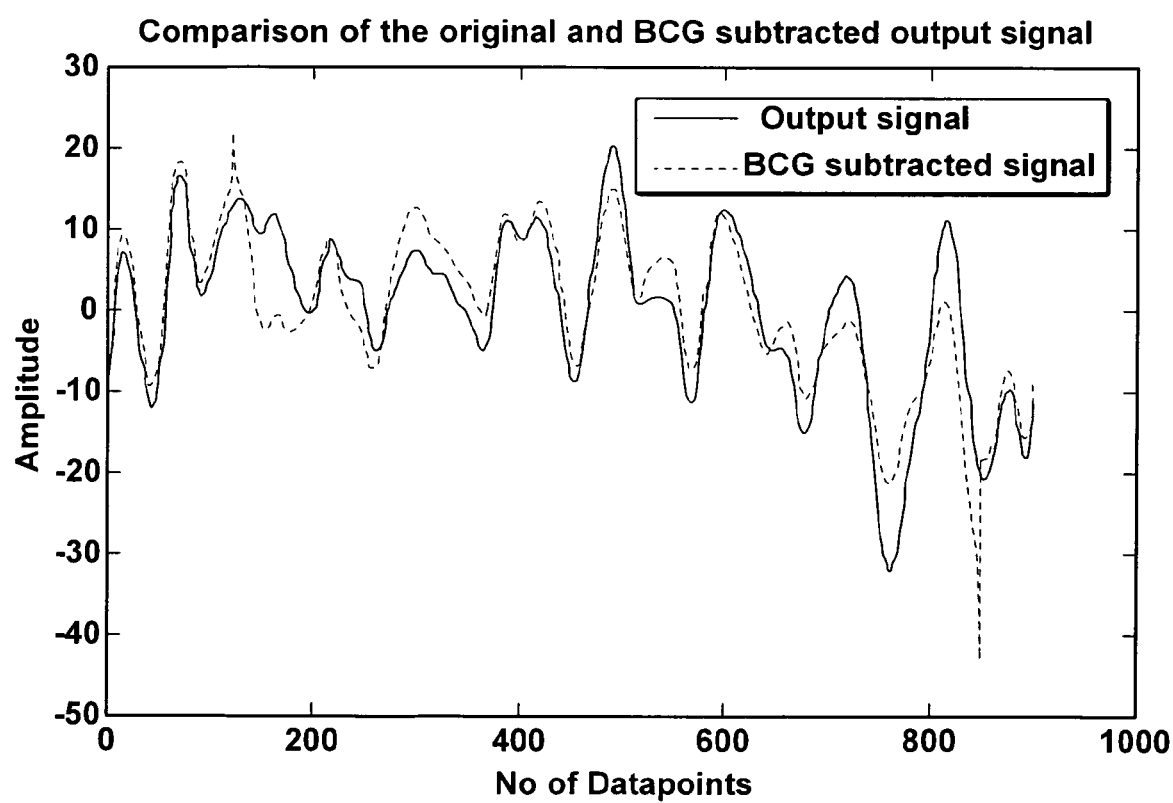
FIG. 16(c) is a plot of outputs of the original and BCG subtracted signals from FIGS. 16(a) and 16(b) in accord with the present invention.
Figure 16D:
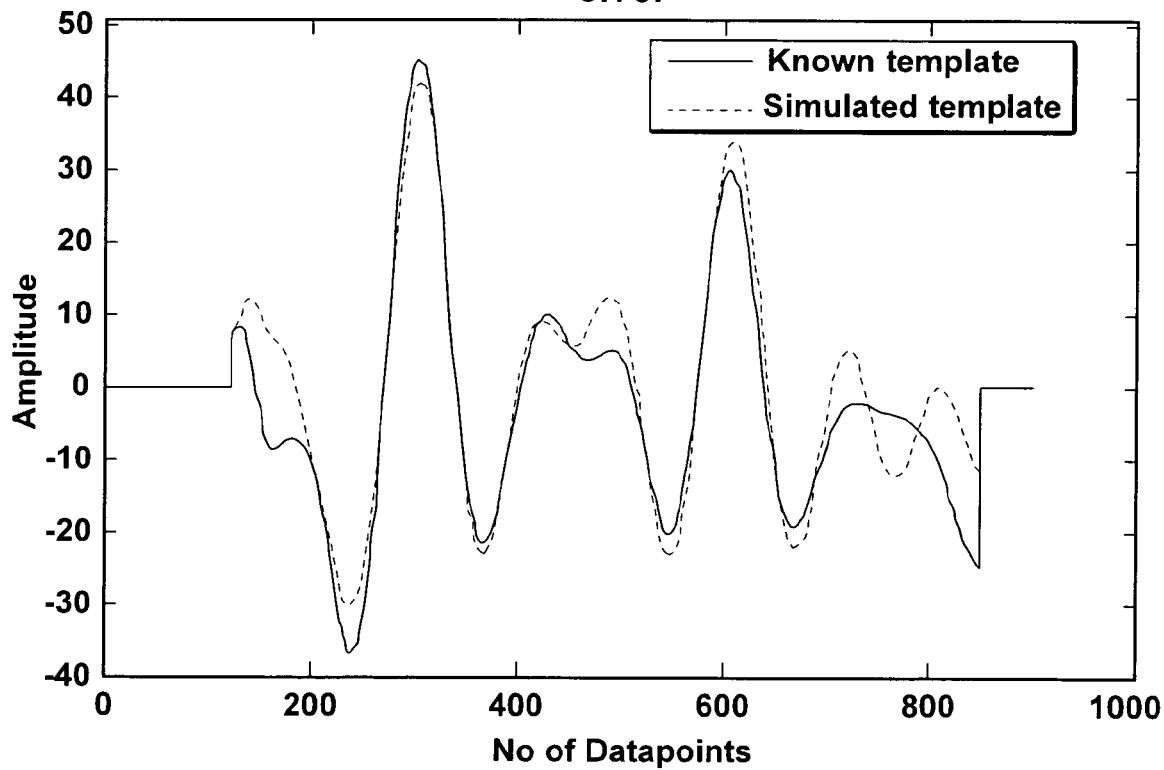
FIG. 16(d) is a plot of known template and simulated template data in accord with the subject invention.
Figure 16E:
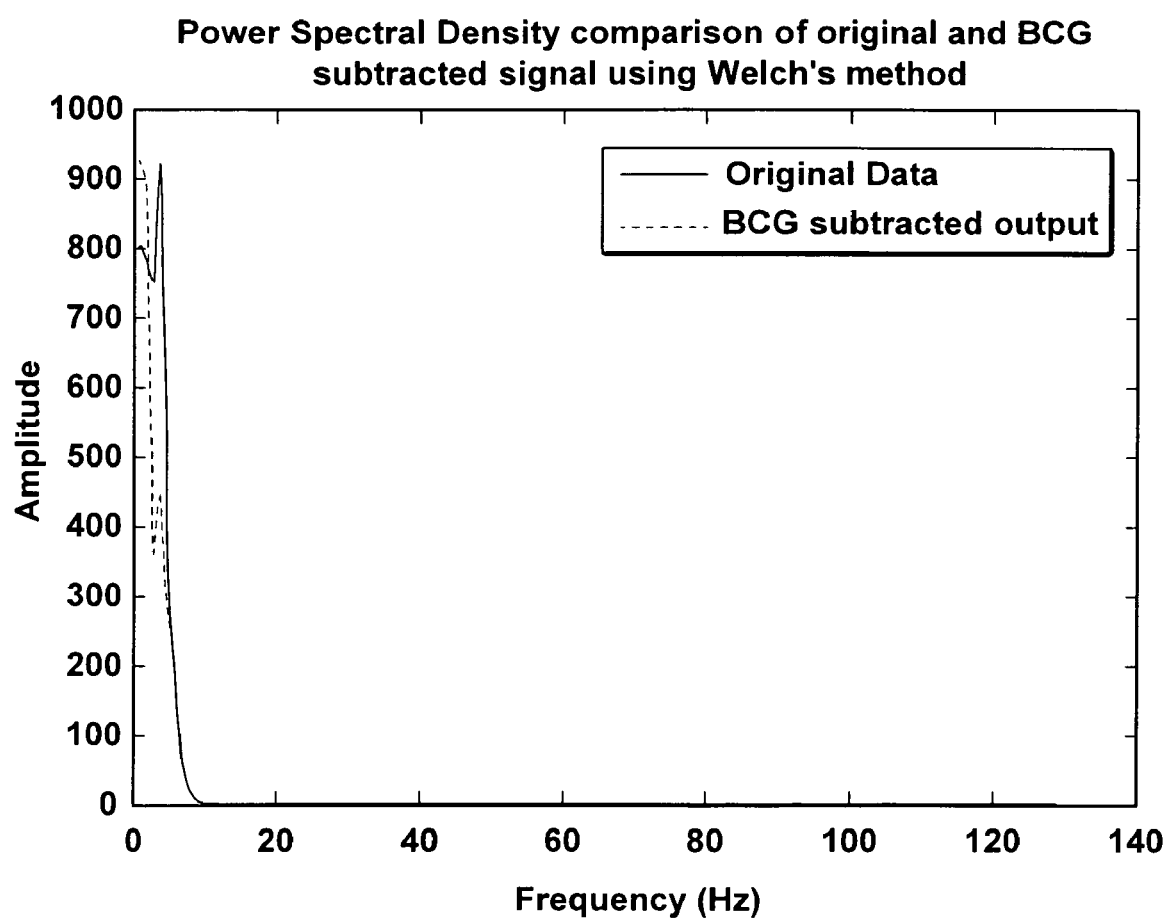
FIG. 16(e) is a plot of comparisons of PSD's of the original and output signals with regard to FIG. 16 in accord with the present invention.
Figure 16F:
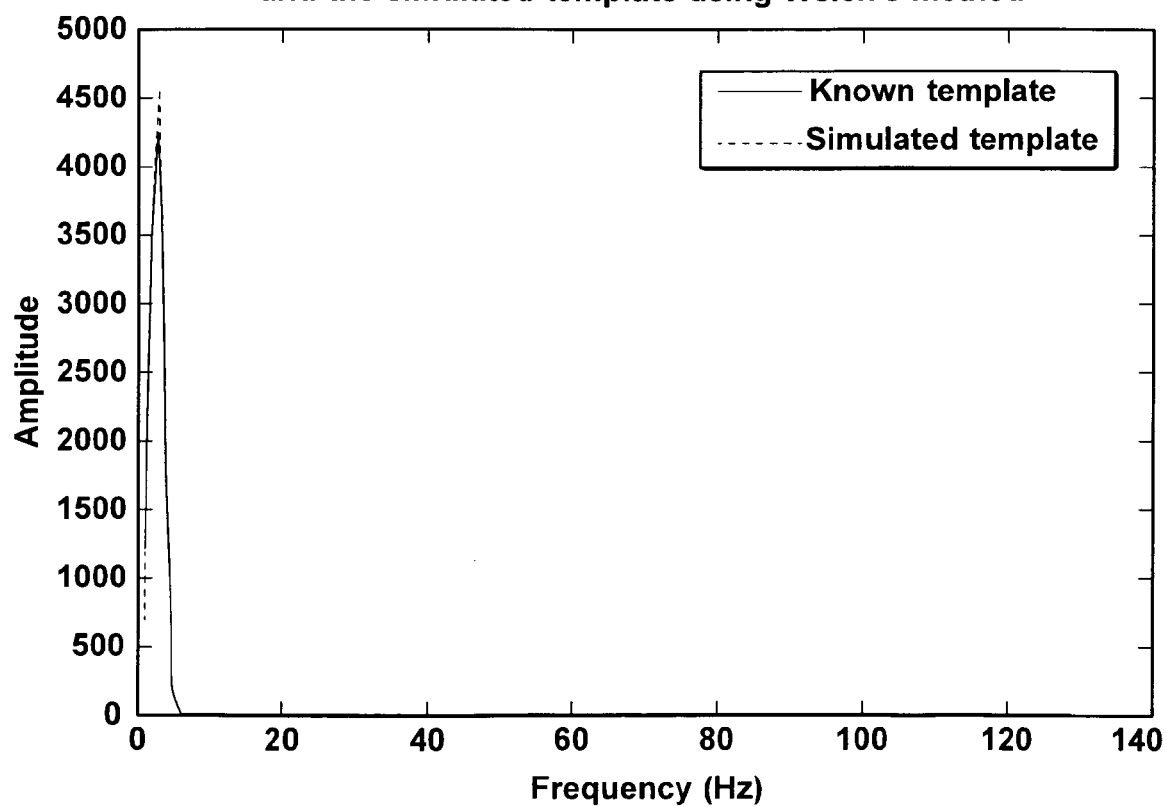
FIG. 16(f) is a plot of comparisons of PSD's of known and simulated BCG templates for FIG. 16 in accord with the present invention.

The fourth test case mentioned above was performed to test the effects of the BCG removal algorithm on alpha waves, particularly because they have overlapping frequency spectra. For this reason, a signal with no BCG and eyes closed (indicating strong alpha) was recorded from a subject. A BCG template was added to this alpha signal and was passed through the BCG removal algorithm. FIG. 16(a) shows the original alpha wave signal (low pass filtered in the range of 0-30 Hz) and FIG. 16(b) shows the BCG, or noise, template added. FIG. 16(c) shows the comparison of the BCG subtracted output with the original input signal, while FIG. 16(d) shows a comparison of the known BCG template and the simulated BCG template found from the algorithm. On observing the results, it was found that there exists some difference between the input signal and the output signal. To compare the results obtained, a power spectral density (PSD) analysis was carried out. FIG. 16(e) shows the PSD's of the original and output signals while FIG. 16(f) shows the PSD's of the known and simulated BCG templates respectively. The PSD's of the input and output signals match closely as can be observed from the FIG. 16(e). A non-parametric test (Wiicoxon's test) was also performed on the data and the 'p' value was found to be 0.7240 (p>0.05) which proves that the differences in the two signals is not significant. This shows the efficiency of the algorithm in eliminating only the BCG noise components.

The foregoing data demonstrates application of a new discrete Hermite transform-based technique for BCG artifact removal from an EEG signal recorded in a MR scanner. The results illustrate use of the Hermite transform method to adaptively prototype the BCG artifact and eliminate the same successfully. The method is computationally simple and rapid. The advantage of applying the transform with a high dilation parameter is that the Hermite functions are able to envelop the entire length of the BCG artifact rather than replicating just the middle peak. An initial comparison of the frequency spectra for EEG with the BCG artifact and without the artifact shows a clear reduction in the magnitude of lower frequency components especially in the 3-14 Hz range. The third test case supports application of the method to identify epileptic spikes. The statistical results obtained in test cases 2 and 4 demonstrate that the algorithm is effective in eliminating only the BCG artifacts and does not have an effect on other EEG signals of interest. All the above results show that the BCG artifact removal algorithm functions efficiently to eliminate only the BCG artifact and not any signals of interest. The method is, therefore, proven to be computationally efficient, resourceful and advantageous as compared to previous methods. More importantly, the developed algorithm is computationally fast enough for real-time implementation.

As shown above, the present invention, in another embodiment, is directed to a method for identifying and removing artifacts from an EEG, including radiofrequency and BCG artifacts, in real-time, to improve critical assessment of data signals. In this regard, the method entails gathering EEG data or signals, and subjecting the same to a detection algorithm in order to scan for BCG artifacts. The data provided herein supports the conclusion that by applying the algorithm for BCG artifact removal using the dilated discrete Hermite transform coefficients, the BCG can be accurately modeled and any artifacts subtracted from the underlying EEG on a beat-by-beat basis. The recovered EEG is an artifact-free signal. In addition, the process can be accomplished in real-time.

The present invention is not limited to application only for ECG and EEG signal data. Rather, the present invention can be applied to a wide variety of measured signal data in the manner shown to identify abnormalities, and therefore is useful in the tracking and diagnosis of the same in real-time. Although the invention has been described in detail with particular reference to certain embodiments, other embodiments can achieve the same results. The method applies to any signal measurement technique wherein electrical data is gathered from a patient or source and is susceptible to distortion by factors generated either by the patient or by any external source. Variations and modifications of the present invention will be obvious to those skilled in the art and the present invention is intended to cover in the appended claims all such modifications and equivalents.

The invention claimed is:

1. A method for identifying a biomedically notable digital signal of interest comprising the steps of: (a) obtaining a digital electronic signal; (b) isolating an interval of interest including the notable digital signal; (c) applying a dilated digital Hermite transform to the interval of interest to represent the shape of the signal in the interval of interest in a set of orthogonal vectors; and (d) modifying the transform to identify an underlying digital signal which is the notable digital signal of interest.

2. The method of claim 1 wherein the set of vectors are derived from a symmetrical tridiagonal matrix.

3. The method according to claim 2 wherein the notable digital signal of interest is in the form of at least one of an EEG, an ECG, an EMG, and an EOG.

4. The method according to claim 1 wherein the modification of step (d) is based on shape content of the underlying signal as revealed by the digital Hermite transform.

5. The method according to claim 1 wherein the steps are performed in real-time.

6. The method according to claim 1 wherein the modification of step (d) includes the removal of noise to isolate the notable digital signal of interest.

7. The method according to claim 1 wherein the notable digital signal of interest is part of an EEG and the modification of step (d) includes the removal of BCG artifacts.

8. The method according to claim 1 further comprising the steps of:
provinding a computer system having at least one power source, at least one input device, at least one display, and at least one memory device;
calculating the dilated digital Hermite transform using the computer system; and
modifying the notable signal using the dilated digital Hermite transform calculated at the calculating step.

9. A method for monitoring/detecting abnormalities in an ECG, the method comprising the steps of: (a) gathering at least one ECG; (b) subjecting the at least one ECG to a QRS detection algorithm in order to scan for R-peak location; (c) calculating a digital Hermite transform corresponding to the individual ECG complexes from each individual ECG to represent the shape of the ECG in a set of orthogonal vectors; and (d) subjecting the Hermite transform coefficients to a Neural Network in order to determine the present and/or absence of ECG abnormalities.

10. The method according to claim 9 wherein the digital Hermite transform coefficients of step (c) are calculated by a simple dot product.

11. The method according to claim 9 wherein the steps are performed in real-time.

12. The method according to claim 9 wherein the ECG abnormalities being monitored are associated with cardiac ischemia.

13. The method according to claim 12 wherein the Neural Network outputs the presence or absence of ST segment changes, T wave changes, beat classification, ischemia, or a combination of one or more thereof.

14. The method according to claim 9 further comprising the steps of:
providing a computer system having at least one power source, at least one input device, at least one display, and at least one memory device; and
configuring the computer system to act as said Neural Network.

15. A method for identifying and removing artifacts from an EEG in real-time to improve critical assessment of data signals, the method comprising: (a) gathering at least one EEG over several heart beats; (b) subjecting the at least one EEG to a detection algorithm in order to scan for artifacts; (c) applying the algorithm for artifact removal using dilated digital Hermite transform coefficients to adaptively prototype the artifact accurately; (d) subtracting the artifact from the underlying EEG on a beat-by-beat basis; and (e) recovering an artifact-free signal, the method being completed in real-time.

16. The method according to claim 15 wherein the artifacts are at least one of a radiofrequency artifact and a BCG artifact.

17. The method according to claim 15 wherein the artifact removal of step (c) is based on shape content of the underlying EEG as revealed by the digital Hermite transform.

18. The method according to claim 15 further comprising the steps of:
providing a computer system having at least one power source, at least one input device, at least one display, and at least one memory device;
calculating the dilated digital Hermite transform using the computer system; and
modifying the EEG signal using the dilated digital Hermite transform calculated at the calculating step.

19. A method for the application of dilated digital Hermite functions to biomedical data, the method comprising the steps of (a) gathering data comprising at least one electronic-based measured signal; (b) expanding the electronic-based measured signal by application of a dilated digital Hermite transform to represent the shape of the measured signal in a set of orthogonal vectors; (c) extracting at least one feature using the transform relating to the electronic-based measured signal; and (d) generating a new version of the electronic-based measured signal that includes only an underlying signal of interest present in the electronic-based measured signal of step (a) without unwanted noise.

20. The method according to claim 19 wherein the extracted features of step (c) include noise, artifacts, or abnormalities.

21. The method according to claim 19 wherein the set of vectors are derived from a symmetrical tridiagonal matrix.

22. The method according to claim 19 wherein the steps are performed in real-time.

23. The method according to claim 19 further comprising the steps of:
providing a computer system having at least power source, at least one input device, at least one display, and at least one memory device;
calculating the dilated Hermite transform using the computer system; and
modifying the electronic-based measured signal with the dilated Hermite transform calculated at the calculating step.

* * * * *

UNITED STATES PATENT AND TRADEMARK OFFICE
CERTIFICATE OF CORRECTION

| | | |
|---|---|---|
| PATENT NO. | : 8,249,698 B2 | Page 1 of 1 |
| APPLICATION NO. | : 12/062551 | |
| DATED | : August 21, 2012 | |
| INVENTOR(S) | : Dale H. Mugler et al. | |

It is certified that error appears in the above-identified patent and that said Letters Patent is hereby corrected as shown below:

In the Claims

Column 18, line 47, "at least power" should read --at least one power--.

Signed and Sealed this
Twenty-ninth Day of April, 2014

Michelle K. Lee
*Deputy Director of the United States Patent and Trademark Office*